(12) United States Patent
Jiang et al.

(10) Patent No.: US 11,484,723 B2
(45) Date of Patent: Nov. 1, 2022

(54) ATTACHMENT DEVICES AND ASSOCIATED METHODS OF USE WITH A NERVE STIMULATION CHARGING DEVICE

(71) Applicant: Axonics, Inc., Irvine, CA (US)

(72) Inventors: Guangqiang Jiang, Irvine, CA (US); Dennis Schroeder, Los Angeles, CA (US); Raymond W. Cohen, Irvine, CA (US)

(73) Assignee: AXONICS, INC., Irvine, CA (US)

( * ) Notice: Subject to any disclaimer, the term of this patent is extended or adjusted under 35 U.S.C. 154(b) by 82 days.

(21) Appl. No.: 16/871,738

(22) Filed: May 11, 2020

(65) Prior Publication Data

US 2020/0338357 A1 Oct. 29, 2020

Related U.S. Application Data

(62) Division of application No. 14/992,977, filed on Jan. 11, 2016, now Pat. No. 10,682,521.

(60) Provisional application No. 62/101,884, filed on Jan. 9, 2015.

(51) Int. Cl.
*A61N 1/378* (2006.01)

(52) U.S. Cl.
CPC .................. *A61N 1/3787* (2013.01)

(58) Field of Classification Search
None
See application file for complete search history.

(56) References Cited

U.S. PATENT DOCUMENTS

| 3,057,356 | A | 10/1962 | Greatbatch |
| 3,348,548 | A | 10/1967 | Chardack |
| 3,646,940 | A | 3/1972 | Timm et al. |
| 3,824,129 | A | 7/1974 | Fagan, Jr. |
| 3,825,015 | A | 7/1974 | Berkovits |

(Continued)

FOREIGN PATENT DOCUMENTS

| AT | 520440 | 9/2011 |
| AU | 4664800 | 11/2000 |

(Continued)

OTHER PUBLICATIONS

US 9,601,939 B2, 03/2017, Cong et al. (withdrawn)

(Continued)

*Primary Examiner* — Erica S Lee
(74) *Attorney, Agent, or Firm* — Kilpatrick Townsend & Stockton LLP

(57) ABSTRACT

Methods for transcutaneous charging of an implanted device may include removably coupling a charging device with a carrier having adhesive tabs, the tabs being movable between a first position configured to be spaced away from a skin surface and a second position configured to be urged against the skin surface; engaging a bottom surface of the charging device at least partially against the skin surface with the tabs in the first position; positioning the charging device until it is at least partially positioned over or proximate the implanted medical device; and moving the tabs to the second position so that respective adhesive surfaces of the tabs contact and adhere to the skin of the patient sufficiently to support the charging device coupled with the carrier for a duration of time sufficient to charge the implanted device.

22 Claims, 23 Drawing Sheets

(56) References Cited

U.S. PATENT DOCUMENTS

| | | |
|---|---|---|
| 3,888,260 A | 6/1975 | Fischell |
| 3,902,501 A | 9/1975 | Citron et al. |
| 3,939,843 A | 2/1976 | Smyth |
| 3,942,535 A * | 3/1976 | Schulman .............. H01M 10/46 607/33 |
| 3,970,912 A | 7/1976 | Hoffman |
| 3,995,623 A | 12/1976 | Blake et al. |
| 4,019,518 A | 4/1977 | Maurer et al. |
| 4,044,774 A | 8/1977 | Corbin et al. |
| 4,082,097 A | 4/1978 | Mann et al. |
| 4,141,365 A | 2/1979 | Fischell et al. |
| 4,166,469 A | 9/1979 | Littleford |
| 4,269,198 A | 5/1981 | Stokes |
| 4,285,347 A | 8/1981 | Hess |
| 4,340,062 A | 7/1982 | Thompson et al. |
| 4,379,462 A | 4/1983 | Borkan et al. |
| 4,407,303 A | 10/1983 | Akerstrom |
| 4,437,475 A | 3/1984 | White |
| 4,512,351 A | 4/1985 | Pohndorf |
| 4,550,731 A | 11/1985 | Batina et al. |
| 4,558,702 A | 12/1985 | Barreras et al. |
| 4,654,880 A | 3/1987 | Sontag |
| 4,662,382 A | 5/1987 | Sluetz et al. |
| 4,719,919 A | 1/1988 | Marchosky et al. |
| 4,721,118 A | 1/1988 | Harris |
| 4,722,353 A | 2/1988 | Sluetz |
| 4,744,371 A | 5/1988 | Harris |
| 4,800,898 A | 1/1989 | Hess et al. |
| 4,848,352 A | 7/1989 | Pohndorf et al. |
| 4,860,446 A | 8/1989 | Lessar et al. |
| 4,957,118 A | 9/1990 | Erlebacher |
| 4,989,617 A | 2/1991 | Memberg et al. |
| 5,012,176 A | 4/1991 | Laforge |
| 5,052,407 A | 10/1991 | Hauser et al. |
| 5,197,466 A | 3/1993 | Marchosky et al. |
| 5,204,611 A | 4/1993 | Nor et al. |
| 5,255,691 A | 10/1993 | Otten |
| 5,257,634 A | 11/1993 | Kroll |
| 5,342,408 A | 8/1994 | Decoriolis et al. |
| 5,394,877 A * | 3/1995 | Orr ......................... A61B 5/25 600/459 |
| 5,439,485 A | 8/1995 | Mar et al. |
| 5,476,499 A | 12/1995 | Hirschberg |
| 5,484,445 A | 1/1996 | Knuth |
| 5,571,148 A | 11/1996 | Loeb et al. |
| 5,592,070 A | 1/1997 | Mino |
| 5,637,981 A | 6/1997 | Nagai et al. |
| 5,676,162 A | 10/1997 | Larson, Jr. et al. |
| 5,690,693 A | 11/1997 | Wang et al. |
| 5,702,428 A | 12/1997 | Tippey et al. |
| 5,702,431 A | 12/1997 | Wang et al. |
| 5,712,795 A | 1/1998 | Layman et al. |
| 5,713,939 A | 2/1998 | Nedungadi et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,871,532 A | 2/1999 | Schroeppel |
| 5,876,423 A | 3/1999 | Braun |
| 5,902,331 A | 5/1999 | Bonner et al. |
| 5,948,006 A | 9/1999 | Mann |
| 5,949,632 A | 9/1999 | Barreras, Sr. et al. |
| 5,957,965 A | 9/1999 | Moumane et al. |
| 5,991,665 A | 11/1999 | Wang et al. |
| 6,027,456 A | 2/2000 | Feler et al. |
| 6,035,237 A | 3/2000 | Schulman et al. |
| 6,052,624 A | 4/2000 | Mann |
| 6,055,456 A | 4/2000 | Gerber |
| 6,057,513 A | 5/2000 | Ushikoshi et al. |
| 6,067,474 A | 5/2000 | Schulman et al. |
| 6,075,339 A | 6/2000 | Reipur et al. |
| 6,076,017 A | 6/2000 | Taylor et al. |
| 6,081,097 A | 6/2000 | Seri et al. |
| 6,083,247 A | 7/2000 | Rutten et al. |
| 6,104,957 A | 8/2000 | Alo et al. |
| 6,104,960 A | 8/2000 | Duysens et al. |
| 6,138,681 A | 10/2000 | Chen et al. |
| 6,165,180 A | 12/2000 | Cigaina et al. |
| 6,166,518 A | 12/2000 | Echarri et al. |
| 6,169,387 B1 | 1/2001 | Kaib |
| 6,172,556 B1 | 1/2001 | Prentice |
| 6,178,353 B1 | 1/2001 | Griffith et al. |
| 6,181,105 B1 | 1/2001 | Cutolo et al. |
| 6,191,365 B1 | 2/2001 | Avellanet |
| 6,208,894 B1 | 3/2001 | Schulman et al. |
| 6,212,430 B1 | 4/2001 | Kung |
| 6,212,431 B1 | 4/2001 | Hahn et al. |
| 6,221,513 B1 | 4/2001 | Lasater |
| 6,227,204 B1 | 5/2001 | Baumann et al. |
| 6,243,608 B1 | 6/2001 | Pauly et al. |
| 6,246,911 B1 | 6/2001 | Seligman |
| 6,249,703 B1 | 6/2001 | Stanton et al. |
| 6,265,789 B1 | 7/2001 | Honda et al. |
| 6,275,737 B1 | 8/2001 | Mann |
| 6,278,258 B1 | 8/2001 | Echarri et al. |
| 6,305,381 B1 | 10/2001 | Weijand et al. |
| 6,306,100 B1 | 10/2001 | Prass |
| 6,315,721 B2 | 11/2001 | Schulman et al. |
| 6,316,909 B1 | 11/2001 | Honda et al. |
| 6,321,118 B1 | 11/2001 | Hahn |
| 6,327,504 B1 | 12/2001 | Dolgin et al. |
| 6,354,991 B1 | 3/2002 | Gross et al. |
| 6,360,750 B1 | 3/2002 | Gerber et al. |
| 6,381,496 B1 | 4/2002 | Meadows et al. |
| 6,393,325 B1 | 5/2002 | Mann et al. |
| 6,438,423 B1 | 8/2002 | Rezai et al. |
| 6,442,434 B1 | 8/2002 | Zarinetchi et al. |
| 6,453,198 B1 | 9/2002 | Torgerson et al. |
| 6,466,817 B1 | 10/2002 | Kaula et al. |
| 6,473,652 B1 | 10/2002 | Sarwal et al. |
| 6,500,141 B1 | 12/2002 | Irion et al. |
| 6,505,075 B1 | 1/2003 | Weiner |
| 6,505,077 B1 | 1/2003 | Kast et al. |
| 6,510,347 B2 | 1/2003 | Borkan |
| 6,516,227 B1 | 2/2003 | Meadows et al. |
| 6,517,227 B2 | 2/2003 | Stidham et al. |
| 6,542,846 B1 | 4/2003 | Miller et al. |
| 6,553,263 B1 | 4/2003 | Meadows et al. |
| 6,584,355 B2 | 6/2003 | Stessman |
| 6,600,954 B2 | 7/2003 | Cohen et al. |
| 6,609,031 B1 | 8/2003 | Law et al. |
| 6,609,032 B1 | 8/2003 | Woods et al. |
| 6,609,945 B2 | 8/2003 | Jimenez et al. |
| 6,652,449 B1 | 11/2003 | Gross et al. |
| 6,662,051 B1 | 12/2003 | Eraker et al. |
| 6,664,763 B2 | 12/2003 | Echarri et al. |
| 6,685,638 B1 | 2/2004 | Taylor et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mamo et al. |
| 6,972,543 B1 | 12/2005 | Wells et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,127,298 B1 | 10/2006 | He et al. |
| 7,131,996 B2 | 11/2006 | Wasserman et al. |
| 7,142,925 B1 | 11/2006 | Bhadra et al. |
| 7,146,219 B2 | 12/2006 | Sieracki et al. |
| 7,151,914 B2 | 12/2006 | Brewer |
| 7,167,749 B2 | 1/2007 | Biggs et al. |
| 7,167,756 B1 | 1/2007 | Torgerson et al. |
| 7,177,690 B2 | 2/2007 | Woods et al. |
| 7,177,698 B2 | 2/2007 | Klosterman et al. |

(56) References Cited

U.S. PATENT DOCUMENTS

| | | |
|---|---|---|
| 7,181,286 B2 | 2/2007 | Sieracki et al. |
| 7,184,836 B1 | 2/2007 | Meadows et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,028 B2 | 5/2007 | Della Santina et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,239,918 B2 | 7/2007 | Strother et al. |
| 7,245,972 B2 | 7/2007 | Davis |
| 7,286,880 B2 | 10/2007 | Olson et al. |
| 7,295,878 B1 | 11/2007 | Meadows et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,326,181 B2 | 2/2008 | Katims |
| 7,328,068 B2 | 2/2008 | Spinelli et al. |
| 7,330,764 B2 | 2/2008 | Swoyer et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,444,184 B2 | 10/2008 | Boveja et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,486,048 B2 | 2/2009 | Tsukamoto et al. |
| 7,496,404 B2 | 2/2009 | Meadows et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |
| 7,565,203 B2 | 7/2009 | Greenberg et al. |
| 7,574,262 B2 | 8/2009 | Haugland et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,617,002 B2 | 11/2009 | Goetz |
| 7,640,059 B2 | 12/2009 | Forsberg et al. |
| 7,643,880 B2 | 1/2010 | Tanagho et al. |
| 7,650,192 B2 | 1/2010 | Wahlstrand |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,878,207 B2 | 2/2011 | Goetz et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,800 B2 | 8/2011 | Takeda et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,224,460 B2 | 7/2012 | Schleicher et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,467,875 B2 | 6/2013 | Bennett et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,544,322 B2 | 10/2013 | Minami et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,706,254 B2 | 4/2014 | Vamos et al. |
| 8,725,262 B2 | 5/2014 | Olson et al. |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,855,767 B2 | 10/2014 | Faltys et al. |
| 8,918,174 B2 | 12/2014 | Woods et al. |
| 8,954,148 B2 | 2/2015 | Labbe et al. |
| 8,989,861 B2 | 3/2015 | Su et al. |

(56) References Cited

U.S. PATENT DOCUMENTS

| | | |
|---|---|---|
| 9,044,592 B2 | 6/2015 | Imran et al. |
| 9,050,473 B2 | 6/2015 | Woods et al. |
| 9,089,712 B2 | 7/2015 | Joshi et al. |
| 9,108,063 B2 | 8/2015 | Olson et al. |
| 9,144,680 B2 | 9/2015 | Kaula et al. |
| 9,149,635 B2 | 10/2015 | Denison et al. |
| 9,155,885 B2 | 10/2015 | Wei et al. |
| 9,166,321 B2 | 10/2015 | Smith et al. |
| 9,168,374 B2 | 10/2015 | Su |
| 9,192,763 B2 | 11/2015 | Gerber et al. |
| 9,197,173 B2 | 11/2015 | Denison et al. |
| 9,199,075 B1 | 12/2015 | Westlund |
| 9,205,255 B2 | 12/2015 | Strother et al. |
| 9,209,634 B2 | 12/2015 | Cottrill et al. |
| 9,216,294 B2 | 12/2015 | Bennett et al. |
| 9,227,055 B2 | 1/2016 | Wahlstrand et al. |
| 9,227,076 B2 | 1/2016 | Sharma et al. |
| 9,238,135 B2 | 1/2016 | Goetz et al. |
| 9,240,630 B2 | 1/2016 | Joshi |
| 9,242,090 B2 | 1/2016 | Atalar et al. |
| 9,244,898 B2 | 1/2016 | Vamos et al. |
| 9,248,292 B2 | 2/2016 | Trier et al. |
| 9,259,578 B2 | 2/2016 | Torgerson et al. |
| 9,259,582 B2 | 2/2016 | Joshi et al. |
| 9,265,958 B2 | 2/2016 | Joshi et al. |
| 9,270,134 B2 | 2/2016 | Gaddam et al. |
| 9,272,140 B2 | 3/2016 | Gerber et al. |
| 9,283,394 B2 | 3/2016 | Whitehurst et al. |
| 9,295,851 B2 | 3/2016 | Gordon et al. |
| 9,308,022 B2 | 4/2016 | Chitre et al. |
| 9,308,382 B2 | 4/2016 | Strother et al. |
| 9,314,616 B2 | 4/2016 | Wells et al. |
| 9,320,899 B2 | 4/2016 | Parramon et al. |
| 9,333,339 B2 | 5/2016 | Weiner |
| 9,352,148 B2 | 5/2016 | Stevenson et al. |
| 9,352,150 B2 | 5/2016 | Stevenson et al. |
| 9,358,039 B2 | 6/2016 | Kimmel et al. |
| 9,364,658 B2 | 6/2016 | Wechter |
| 9,375,574 B2 | 6/2016 | Kaula et al. |
| 9,393,423 B2 | 7/2016 | Parramon et al. |
| 9,399,137 B2 | 7/2016 | Parker et al. |
| 9,409,020 B2 | 8/2016 | Parker |
| 9,415,211 B2 | 8/2016 | Bradley et al. |
| 9,427,571 B2 | 8/2016 | Sage et al. |
| 9,427,573 B2 | 8/2016 | Gindele et al. |
| 9,433,783 B2 | 9/2016 | Wei et al. |
| 9,436,481 B2 | 9/2016 | Drew |
| 9,446,245 B2 | 9/2016 | Grill et al. |
| 9,463,324 B2 | 10/2016 | Olson et al. |
| 9,468,755 B2 | 10/2016 | Westlund et al. |
| 9,471,753 B2 | 10/2016 | Kaula et al. |
| 9,480,846 B2 | 11/2016 | Strother et al. |
| 9,492,672 B2 | 11/2016 | Vamos et al. |
| 9,492,675 B2 | 11/2016 | Torgerson et al. |
| 9,492,678 B2 | 11/2016 | Chow |
| 9,498,628 B2 | 11/2016 | Kaemmerer et al. |
| 9,502,754 B2 | 11/2016 | Zhao et al. |
| 9,504,830 B2 | 11/2016 | Kaula et al. |
| 9,522,282 B2 | 12/2016 | Chow et al. |
| 9,592,389 B2 | 3/2017 | Moffitt |
| 9,610,449 B2 | 4/2017 | Kaula et al. |
| 9,615,744 B2 | 4/2017 | Denison et al. |
| 9,623,257 B2 | 4/2017 | Olson et al. |
| 9,636,497 B2 | 5/2017 | Bradley et al. |
| 9,643,004 B2 | 5/2017 | Gerber |
| 9,653,935 B2 | 5/2017 | Cong et al. |
| 9,656,074 B2 | 5/2017 | Simon et al. |
| 9,656,076 B2 | 5/2017 | Trier et al. |
| 9,656,089 B2 | 5/2017 | Yip et al. |
| 9,675,809 B2 | 6/2017 | Chow |
| 9,687,649 B2 | 6/2017 | Thacker |
| 9,707,405 B2 | 7/2017 | Shishilla et al. |
| 9,713,706 B2 | 7/2017 | Gerber |
| 9,717,900 B2 | 8/2017 | Swoyer et al. |
| 9,724,526 B2 | 8/2017 | Strother et al. |
| 9,731,116 B2 | 8/2017 | Chen |
| 9,737,704 B2 | 8/2017 | Wahlstrand et al. |
| 9,744,347 B2 | 8/2017 | Chen et al. |
| 9,750,930 B2 | 9/2017 | Chen |
| 9,757,555 B2 | 9/2017 | Novotny et al. |
| 9,764,147 B2 | 9/2017 | Torgerson |
| 9,767,255 B2 | 9/2017 | Kaula et al. |
| 9,776,002 B2 | 10/2017 | Parker et al. |
| 9,776,006 B2 | 10/2017 | Parker et al. |
| 9,776,007 B2 | 10/2017 | Kaula et al. |
| 9,782,596 B2 | 10/2017 | Vamos et al. |
| 9,814,884 B2 | 11/2017 | Parker et al. |
| 9,821,112 B2 | 11/2017 | Olson et al. |
| 9,827,415 B2 | 11/2017 | Stevenson et al. |
| 9,827,424 B2 | 11/2017 | Kaula et al. |
| 9,833,614 B1 | 12/2017 | Gliner |
| 9,849,278 B2 | 12/2017 | Spinelli et al. |
| 9,855,438 B2 | 1/2018 | Parramon et al. |
| 9,872,988 B2 | 1/2018 | Kaula et al. |
| 9,878,165 B2 | 1/2018 | Wilder et al. |
| 9,878,168 B2 | 1/2018 | Shishilla et al. |
| 9,882,420 B2 | 1/2018 | Cong et al. |
| 9,884,198 B2 | 2/2018 | Parker |
| 9,889,292 B2 | 2/2018 | Gindele et al. |
| 9,889,293 B2 | 2/2018 | Siegel et al. |
| 9,889,306 B2 | 2/2018 | Stevenson et al. |
| 9,895,532 B2 | 2/2018 | Kaula et al. |
| 9,899,778 B2 | 2/2018 | Hanson et al. |
| 9,901,284 B2 | 2/2018 | Olsen et al. |
| 9,901,740 B2 | 2/2018 | Drees et al. |
| 9,907,476 B2 | 3/2018 | Bonde et al. |
| 9,907,955 B2 | 3/2018 | Bakker et al. |
| 9,907,957 B2 | 3/2018 | Woods et al. |
| 9,924,904 B2 | 3/2018 | Cong et al. |
| 9,931,513 B2 | 4/2018 | Kelsch et al. |
| 9,931,514 B2 | 4/2018 | Frysz et al. |
| 9,950,171 B2 | 4/2018 | Johanek et al. |
| 9,974,108 B2 | 5/2018 | Polefko |
| 9,974,949 B2 | 5/2018 | Thompson et al. |
| 9,981,121 B2 | 5/2018 | Seifert et al. |
| 9,981,137 B2 | 5/2018 | Eiger |
| 9,987,493 B2 | 6/2018 | Torgerson et al. |
| 9,993,650 B2 | 6/2018 | Seitz et al. |
| 9,999,765 B2 | 6/2018 | Stevenson |
| 10,004,910 B2 | 6/2018 | Gadagkar et al. |
| 10,016,596 B2 | 7/2018 | Stevenson et al. |
| 10,027,157 B2 | 7/2018 | Labbe et al. |
| 10,045,764 B2 | 8/2018 | Scott et al. |
| 10,046,164 B2 | 8/2018 | Gerber |
| 10,047,782 B2 | 8/2018 | Sage et al. |
| 10,052,490 B2 | 8/2018 | Kaula et al. |
| 10,065,044 B2 | 9/2018 | Sharma et al. |
| 10,071,247 B2 | 9/2018 | Childs |
| 10,076,661 B2 | 9/2018 | Wei et al. |
| 10,076,667 B2 | 9/2018 | Kaula et al. |
| 10,083,261 B2 | 9/2018 | Kaula et al. |
| 10,086,191 B2 | 10/2018 | Bonde et al. |
| 10,086,203 B2 | 10/2018 | Kaemmerer |
| 10,092,747 B2 | 10/2018 | Sharma et al. |
| 10,092,749 B2 | 10/2018 | Stevenson et al. |
| 10,095,837 B2 | 10/2018 | Corey et al. |
| 10,099,051 B2 | 10/2018 | Stevenson et al. |
| 10,103,559 B2 | 10/2018 | Cottrill et al. |
| 10,109,844 B2 | 10/2018 | Dai et al. |
| 10,118,037 B2 | 11/2018 | Kaula et al. |
| 10,124,164 B2 | 11/2018 | Stevenson et al. |
| 10,124,171 B2 | 11/2018 | Kaula et al. |
| 10,124,179 B2 | 11/2018 | Norton et al. |
| 10,141,545 B2 | 11/2018 | Kraft et al. |
| 10,173,062 B2 | 1/2019 | Parker |
| 10,179,241 B2 | 1/2019 | Walker et al. |
| 10,179,244 B2 | 1/2019 | Lebaron et al. |
| 10,183,162 B2 | 1/2019 | Johnson et al. |
| 10,188,857 B2 | 1/2019 | North et al. |
| 10,195,419 B2 | 2/2019 | Shiroff et al. |
| 10,206,710 B2 | 2/2019 | Kern et al. |
| 10,213,229 B2 | 2/2019 | Chitre et al. |
| 10,220,210 B2 | 3/2019 | Walker et al. |
| 10,226,617 B2 | 3/2019 | Finley et al. |

(56) References Cited

U.S. PATENT DOCUMENTS

| | | |
|---|---|---|
| 10,226,636 B2 | 3/2019 | Gaddam et al. |
| 10,236,709 B2 | 3/2019 | Decker et al. |
| 10,238,863 B2 | 3/2019 | Gross et al. |
| 10,238,877 B2 | 3/2019 | Kaula et al. |
| 10,244,956 B2 | 4/2019 | Kane |
| 10,245,434 B2 | 4/2019 | Kaula et al. |
| 10,258,800 B2 | 4/2019 | Perryman et al. |
| 10,265,532 B2 | 4/2019 | Carcieri et al. |
| 10,277,055 B2 | 4/2019 | Peterson et al. |
| 10,293,168 B2 | 5/2019 | Bennett et al. |
| 10,328,253 B2 | 6/2019 | Wells |
| 10,363,419 B2 | 7/2019 | Simon et al. |
| 10,369,275 B2 | 8/2019 | Olson et al. |
| 10,369,370 B2 | 8/2019 | Shishilla et al. |
| 10,376,701 B2 | 8/2019 | Kaula et al. |
| 10,448,889 B2 | 10/2019 | Gerber et al. |
| 10,456,574 B2 | 10/2019 | Chen et al. |
| 10,471,262 B2 | 11/2019 | Perryman et al. |
| 10,485,970 B2 | 11/2019 | Gerber et al. |
| 10,493,282 B2 | 12/2019 | Caparso et al. |
| 10,493,287 B2 | 12/2019 | Yoder et al. |
| 10,561,835 B2 | 2/2020 | Gerber |
| 10,682,521 B2 | 6/2020 | Guangqiang et al. |
| 2002/0040185 A1 | 4/2002 | Atalar et al. |
| 2002/0051550 A1 | 5/2002 | Leysieffer |
| 2002/0051551 A1 | 5/2002 | Leysieffer et al. |
| 2002/0140399 A1 | 10/2002 | Echarri et al. |
| 2002/0177884 A1 | 11/2002 | Ahn et al. |
| 2003/0114899 A1 | 6/2003 | Woods et al. |
| 2003/0212440 A1 | 11/2003 | Boveja |
| 2004/0015208 A1 | 1/2004 | Haugland et al. |
| 2004/0098068 A1 | 5/2004 | Carbunaru et al. |
| 2004/0210290 A1 | 10/2004 | Omar-Pasha |
| 2004/0250820 A1 | 12/2004 | Forsell |
| 2004/0267137 A1 | 12/2004 | Peszynski et al. |
| 2004/0267332 A1 | 12/2004 | Kast et al. |
| 2005/0004619 A1 | 1/2005 | Wahlstrand et al. |
| 2005/0004621 A1 | 1/2005 | Boveja et al. |
| 2005/0021108 A1 | 1/2005 | Klosterman et al. |
| 2005/0075693 A1 | 4/2005 | Toy et al. |
| 2005/0075694 A1 | 4/2005 | Schmeling et al. |
| 2005/0075696 A1 | 4/2005 | Forsberg et al. |
| 2005/0075697 A1* | 4/2005 | Olson .................. A61N 1/3787 607/61 |
| 2005/0075698 A1 | 4/2005 | Phillips et al. |
| 2005/0075699 A1 | 4/2005 | Olson et al. |
| 2005/0075700 A1 | 4/2005 | Schommer et al. |
| 2005/0104577 A1 | 5/2005 | Matei et al. |
| 2005/0187590 A1 | 8/2005 | Boveja et al. |
| 2005/0245839 A1* | 11/2005 | Stivoric ............... A61B 5/0008 600/549 |
| 2005/0245996 A1 | 11/2005 | Phillips et al. |
| 2006/0142822 A1 | 6/2006 | Tulgar |
| 2006/0149345 A1 | 7/2006 | Boggs et al. |
| 2006/0200205 A1 | 9/2006 | Haller |
| 2006/0206166 A1 | 9/2006 | Weiner |
| 2006/0253076 A1* | 11/2006 | Butts .................. A61M 39/0247 604/167.06 |
| 2007/0032836 A1 | 2/2007 | Thrope et al. |
| 2007/0228273 A1 | 10/2007 | Sun et al. |
| 2007/0239224 A1 | 10/2007 | Bennett et al. |
| 2007/0257636 A1 | 11/2007 | Phillips et al. |
| 2007/0265675 A1 | 11/2007 | Lund et al. |
| 2007/0293801 A1* | 12/2007 | May .................... A61F 13/0203 602/54 |
| 2007/0293914 A1 | 12/2007 | Woods et al. |
| 2008/0065182 A1 | 3/2008 | Strother et al. |
| 2008/0132969 A1 | 6/2008 | Bennett et al. |
| 2008/0154335 A1 | 6/2008 | Thrope et al. |
| 2008/0161874 A1 | 7/2008 | Bennett et al. |
| 2008/0183236 A1 | 7/2008 | Gerber |
| 2008/0288025 A1* | 11/2008 | Peterson ............... A61N 1/3787 607/60 |
| 2009/0082835 A1 | 3/2009 | Jaax et al. |
| 2010/0076254 A1 | 3/2010 | Jimenez et al. |
| 2010/0076534 A1 | 3/2010 | Mock |
| 2010/0100158 A1 | 4/2010 | Rope et al. |
| 2010/0174250 A1* | 7/2010 | Hu ........................ A61F 5/4401 604/319 |
| 2010/0331918 A1 | 12/2010 | Digiore et al. |
| 2011/0257701 A1 | 10/2011 | Strother et al. |
| 2011/0282416 A1 | 11/2011 | Hamann et al. |
| 2011/0301667 A1 | 12/2011 | Olson et al. |
| 2012/0041512 A1 | 2/2012 | Weiner |
| 2012/0046712 A1 | 2/2012 | Woods et al. |
| 2012/0130448 A1 | 5/2012 | Woods et al. |
| 2012/0139485 A1 | 6/2012 | Olson et al. |
| 2012/0276854 A1 | 11/2012 | Joshi et al. |
| 2012/0276856 A1 | 11/2012 | Joshi et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0105115 A1 | 5/2013 | Kallmyer et al. |
| 2013/0150925 A1 | 6/2013 | Vamos et al. |
| 2013/0197608 A1 | 8/2013 | Eiger |
| 2013/0207863 A1 | 8/2013 | Joshi |
| 2013/0253614 A1 | 9/2013 | Knifong, Sr. |
| 2013/0310894 A1 | 11/2013 | Trier |
| 2013/0331638 A1 | 12/2013 | Cameron et al. |
| 2013/0331909 A1 | 12/2013 | Gerber |
| 2014/0070761 A1 | 3/2014 | Labbe et al. |
| 2014/0180365 A1 | 6/2014 | Perryman et al. |
| 2014/0194802 A1 | 7/2014 | Check |
| 2014/0222112 A1 | 8/2014 | Fell |
| 2014/0237806 A1 | 8/2014 | Smith et al. |
| 2014/0277270 A1 | 9/2014 | Parramon et al. |
| 2014/0371802 A1 | 12/2014 | Mashiach et al. |
| 2015/0088227 A1 | 3/2015 | Shishilla et al. |
| 2015/0214604 A1 | 7/2015 | Zhao et al. |
| 2016/0199657 A1 | 7/2016 | Jiang et al. |
| 2017/0197079 A1 | 7/2017 | Illegems et al. |
| 2017/0340878 A1 | 11/2017 | Wahlstrand et al. |
| 2018/0021587 A1 | 1/2018 | Strother et al. |
| 2018/0036477 A1 | 2/2018 | Olson et al. |
| 2019/0269918 A1 | 9/2019 | Parker |
| 2019/0351244 A1 | 11/2019 | Shishilla et al. |
| 2019/0358395 A1 | 11/2019 | Olson et al. |

FOREIGN PATENT DOCUMENTS

| | | |
|---|---|---|
| AU | 5123800 | 11/2000 |
| CA | 2371378 | 11/2000 |
| CA | 2554676 | 9/2005 |
| CN | 101234230 | 8/2008 |
| CN | 101259302 A | 9/2008 |
| CN | 101896224 A | 11/2010 |
| CN | 102724017 A | 10/2012 |
| CN | 104487131 | 4/2015 |
| CN | 104511091 A | 4/2015 |
| CN | 105163799 A | 12/2015 |
| CN | 107427685 | 12/2017 |
| DE | 3146182 | 6/1983 |
| EP | 0656218 | 6/1995 |
| EP | 1205004 | 5/2002 |
| EP | 1680182 | 7/2006 |
| EP | 2243509 | 10/2010 |
| EP | 1680182 | 5/2013 |
| EP | 1904153 | 4/2015 |
| EP | 3242721 | 11/2017 |
| EP | 3242721 | 9/2019 |
| ES | 2395128 | 2/2013 |
| HK | 1098715 | 3/2012 |
| JP | 2002253685 | 9/2002 |
| JP | 2007268293 | 10/2007 |
| JP | 4125357 | 7/2008 |
| JP | 2010527569 | 8/2010 |
| JP | 2018501021 | 1/2018 |
| WO | 9820933 | 5/1998 |
| WO | 9918879 | 4/1999 |
| WO | 9934870 | 7/1999 |
| WO | 9942173 | 8/1999 |
| WO | 0056677 | 9/2000 |
| WO | 0065682 | 11/2000 |

(56) References Cited

FOREIGN PATENT DOCUMENTS

| WO | 0069012 | 11/2000 |
|---|---|---|
| WO | 0183029 | 11/2001 |
| WO | 0209808 | 2/2002 |
| WO | 2004021876 | 3/2004 |
| WO | 2004103465 | 12/2004 |
| WO | 2005079295 | 9/2005 |
| WO | 2005081740 | 9/2005 |
| WO | 2008021524 | 2/2008 |
| WO | 2011059565 | 5/2011 |
| WO | 2016112401 | 7/2016 |

OTHER PUBLICATIONS

Ke et al., Design on Experiment on Transcutaneous Energy Charging System in Implantable Medical Device, Chinese Journal of Scientific Instrument, vol. 34, No. 12, Dec. 15, 2013, pp. 2846-2853.
Bu-802a: How Does Rising Internal Resistance Affect Performance? Understanding the Importance of Low Conductivity, BatteryUniversity.com, Available Online at https://batteryuniversity.com/learn/article/rising_internal_resistance, Accessed from Internet on: May 15, 2020, 10 pages.
DOE Handbook: Primer on Lead-Acid Storage Batteries, U.S. Dept. of Energy, Available Online at: htt12s://www.stan dards.doe.gov/standards- documents/I 000/1084-bhdbk-1995/@@images/file, Sep. 1995, 54 pages.
Medical Electrical Equipment—Part 1: General Requirements for Safety, British Standard, BS EN 60601-1:1990-BS5724-1:1989, Mar. 1979, 200 pages.
Summary of Safety and Effectiveness, Medtronic InterStim System for Urinary Control, Apr. 15, 1999, pp. 1-18.
The Advanced Bionics PRECISION™ Spinal Cord Stimulator System, Advanced Bionics Corporation, Apr. 27, 2004, pp. 1-18.
UL Standard for Safety for Medical and Dental Equipment, UL 544, 4th edition, Dec. 30, 1998, 128 pages.
Barnhart et al., "A Fixed-Rate Rechargeable Cardiac Pacemaker", APL Technical Digest, Jan.-Feb. 1970, pp. 2-9.
Benditt et al., "A Combined Atrial/Ventricular Lead for Permanent Dual-Chamber Cardiac Pacing Applications", Chest, vol. 83, No. 6, Jun. 1983, pp. 929-931.
Bosch et al., "Sacral (S3) Segmental Nerve Stimulation as a Treatment for Urge Incontinence in Patients with Detrusor Instability: Results of Chronic Electrical Stimulation Using an Implantable Neural Prosthesis", The Journal of Urology, vol. 154, No. 2, Aug. 1995, pp. 504-507.
Boyce et al., "Research Related to the Development of an Artificial Electrical Stimulator for the Paralyzed Human Bladder: a Review", The Journal of Urology, vol. 91, No. 1, Jan. 1964, pp. 41-51.
Bradley et al., "Further Experience With the Radio Transmitter Receiver Unit for the Neurogenic Bladder", Journal of Neurosurgery, vol. 20, No. 11, Nov. 1963, pp. 953-960.
Broggi et al., "Electrical Stimulation of the Gasserian Ganglion for Facial Pain: Preliminary Results", Acta Neurochirurgica, vol. 39, 1987, pp. 144-146.
Cameron et al., "Effects of Posture on Stimulation Parameters in Spinal Cord Stimulation", Neuromodulation, vol. 1, No. 4, Oct. 1998, pp. 177-183.
Connelly et al., "Atrial Pacing Leads Following Open Heart Surgery: Active or Passive Fixation?", Pacing and Clinical Electrophysiology, vol. 20, No. 10, Oct. 1997, pp. 2429-2433.
Fischell, "The Development of Implantable Medical Devices at the Applied Physics Laboratory", Johns Hopkins APL Technical Digest, vol. 13 No. 1, 1992, pp. 233-243.
Gaunt et al., "Control of Urinary Bladder Function With Devices: Successes and Failures", Progress in Brain Research, vol. 152, 2006, pp. 1-24.
Ghovanloo et al., "A Small Size Large Voltage Compliance Programmable Current Source for Biomedical Implantable Microstimulators", Proceedings of the 25th Annual International Conference of the IEEE EMBS, Sep. 17-21, 2003, pp. 1979-1982.
Helland , "Technical Improvements to be Achieved by the Year 2000: Leads and Connector Technology", Rate Adaptive Cardiac Pacing, Springer Verlag, 1993, pp. 279-292.
Hidefjall , "The Pace of Innovation—Patterns of Innovation in the Cardiac Pacemaker Industry", Linkoping University Press, 1997, 398 pages.
Ishihara et al., "A Comparative Study of Endocardial Pacemaker Leads", Cardiovascular Surgery, Nagoya Ekisaikai Hospital, 1st Dept. of Surgery, Nagoya University School of Medicine, 1981, pp. 132-135.
Jonas et al., "Studies on the Feasibility of Urinary Bladder Evacuation by Direct Spinal Cord Stimulation. I. Parameters of Most Effective Stimulation", Investigative urology, vol. 13, No. 2, 1975, pp. 142-150.
Kakuta et al., "In Vivo Long Term Evaluation of Transcutaneous Energy Transmission for Totally Implantable Artificial Heart", ASAIO Journal, Mar.-Apr. 2000, pp. 1-2.
Kester et al., "Voltage-to-Frequency Converters", Available Online at: https://www.analog.com/media/cn/training-seminars/tutorials/MT-028.pdf, 7 pages.
Lazorthes et al., "Chronic Stimulation of the Gasserian Ganglion for Treatment of Atypical Facial Neuralgia", Pacing and Clinical Electrophysiology, vol. 10, Jan.-Feb. 1987, pp. 257-265.
Lewis et al., "Early Clinical Experience with the Rechargeable Cardiac Pacemaker", The Annals of Thoracic Surgery, vol. 18, No. 5, Nov. 1974, pp. 490-493.
Love et al., "Experimental Testing of a Permanent Rechargeable Cardiac Pacemaker", The Annals of Thoracic Surgery, vol. 17, No. 2, Feb. 1, 1974, pp. 152-156.
Love , "Pacemaker Troubleshooting and Follow-up", Clinical Cardiac Pacing, Defibrillation, and Resynchronization Therapy, Chapter 24, 2007, pp. 1005-1062.
Madigan et al., "Difficulty of Extraction of Chronically Implanted Tined Ventricular Endocardial Leads", Journal of the American College of Cardiology, vol. 3, No. 3, Mar. 1984, pp. 724-731.
Meglio , "Percutaneously Implantable Chronic Electrode for Radiofrequency Stimulation of the Gasserian Ganglion. A Perspective in the Management of Trigeminal Pain", Acta Neurochirurgica, vol. 33, 1984, pp. 521-525.
Meyerson , "Alleviation of Atypical Trigeminal Pain by Stimulation of the Gasserian Ganglion via an Implanted Electrode", Acta Neurochirurgica Suppiementum , vol. 30, 1980, pp. 303-309.
Mitamura et al., "Development of Transcutaneous Energy Transmission System", Available Online at https://www.researchgate.net/publication/312810915 Ch.28, Jan. 1988, pp. 265-270.
Nakamura et al., "Biocompatibility and Practicality Evaluations of Transcutaneous Energy Transmission Unit for the Totally Implantable Artifical Heart System", Journal of Artificial Organs, vol. 27, No. 2, 1998, pp. 347-351.
Nashold et al., "Electromicturition in Paraplegia. Implantation of a Spinal Neuroprosthesis", Arch Surg., vol. 104, Feb. 1972, pp. 195-202.
Painter et al., "Implantation of an Endocardial Tined Lead to Prevent Early Dislodgement", The Journal of Thoracic and Cardiovascular Surgery, vol. 77, No. 2, Feb. 1979, pp. 249-251.
Perez , "Lead-Acid Battery State of Charge vs. Voltage", Available Online at http://www.rencobattery.com/resources/SOC vs-Voltage.pdf, Aug.-Sep. 1993, 5 pages.
Schaldach et al., "A Long-Lived, Reliable, Rechargeable Cardiac Pacemaker", Engineering in Medicine, vol. 1: Advances in Pacemaker Technology, 1975, 34 pages.
Scheuer-Leeser et al., "Polyurethane Leads: Facts and Controversy", PACE, vol. 6, Mar.-Apr. 1983, pp. 454-458.
Smith , "Changing Standards for Medical Equipment", UL 544 and UL 187 vs. UL 2601 ("Smith"), 2002, 8 pages.
Tanagho et al., "Bladder Pacemaker: Scientific Basis and Clinical Future", Urology, vol. 20, No. 6, Dec. 1982, pp. 614-619.
Tanagho , "Neuromodulation and Neurostimulation: Overview and Future Potential", Translational Androl Urol, vol. 1, No. 1, 2012, pp. 44-49.

(56) References Cited

OTHER PUBLICATIONS

Torres et al., "Electrostatic Energy-Harvesting and Battery-Charging CMOS System Prototype", Available Online at: http://rincon mora.gatech.edu/12ublicat/jrnls/tcasi09_hrv_sys.pdf, pp. 1-10.
Young , "Electrical Stimulation of the Trigeminal Nerve Root for the Treatment of Chronic Facial Pain", Journal of Neurosurgery, vol. 83, No. 1, Jul. 1995, pp. 72-78.
U.S. Appl. No. 62/038,122, filed Aug. 15, 2014.
U.S. Appl. No. 62/038,131, filed Aug. 15, 2014.
U.S. Appl. No. 62/041,611, filed Aug. 25, 2014.
U.S. Appl. No. 62/101,666, filed Jan. 9, 2015.
U.S. Appl. No. 62/101,782, filed Jan. 9, 2015.
U.S. Appl. No. 62/101,884, filed Jan. 9, 2015.
U.S. Appl. No. 62/101,888, filed Jan. 9, 2015.
U.S. Appl. No. 62/101,897, filed Jan. 9, 2015.
U.S. Appl. No. 62/101,899, filed Jan. 9, 2015.

\* cited by examiner

ATTACHMENT DEVICES AND ASSOCIATED METHODS OF USE WITH A NERVE STIMULATION CHARGING DEVICE

CROSS-REFERENCES TO RELATED APPLICATIONS

This application is a divisional of U.S. application Ser. No. 14/992,977, filed on Jan. 11, 2016 (now U.S. Patent No. 10,682,521 issued Jun. 16, 2020), which claims the benefit of priority of U.S. Provisional Application No. 62/101,884, filed on Jan. 9, 2015, the entire contents of which are incorporated herein by reference.

The present application is related to U.S. Provisional Patent Application Nos. 62/038,122 filed on Aug. 15, 2014, entitled "Devices and Methods for Anchoring of Neurostimulation Leads"; 62/038,131 filed on Aug. 15, 2014, entitled "External Pulse Generator Device and Associated Methods for Trial Nerve Stimulation"; 62/041,611 filed on Aug. 25, 2014, entitled "Electromyographic Lead Positioning and Stimulation Titration in a Nerve Stimulation System for Treatment of Overactive Bladder, Pain and Other Indicators"; and concurrently filed U.S. Provisional Patent Application Nos. 62/101,888, entitled "Electromyographic Lead Positioning and Stimulation Titration in a Nerve Stimulation System for Treatment of Overactive Bladder"; 62/101,888, entitled "Integrated Electromyographic Clinician Programmer For Use With an Implantable Neurostimulator"; 62/101,897, entitled "Systems and Methods for Neurostimulation Electrode Configurations Based on Neural Localization"; 62/101,666, entitled "Patient Remote and Associated Methods of Use With a Nerve Stimulation System"; and 62/101,782, entitled "Improved Antenna and Methods of Use For an Implantable Nerve Stimulator," all filed on Jan. 9, 2015, each of which is assigned to the same assignee as the present application, and incorporated herein by reference in its entirety for all purposes.

FIELD OF THE INVENTION

The present invention relates to neurostimulation treatment systems and associated devices, as well as methods of treatment, implantation and configuration of such treatment systems.

BACKGROUND OF THE INVENTION

Treatments with implantable neurostimulation systems have become increasingly common in recent years. While such systems have shown promise in treating a number of conditions, effectiveness of treatment may vary considerably between patients. A number of factors may lead to the very different outcomes that patients experience, and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues. Other approaches may also be employed, for example, with one or more electrodes attached to the skin overlying the target nerve structures, implanted in cuffs around a target nerve, or the like. Regardless, the physician will typically seek to establish an appropriate treatment protocol by varying the electrical stimulation that is applied to the electrodes.

Current stimulation electrode placement/implantation techniques and known treatment setting techniques suffer from significant disadvantages. The nerve tissue structures of different patients can be quite different, with the locations and branching of nerves that perform specific functions and/or enervate specific organs being challenging to accurately predict or identify. The electrical properties of the tissue structures surrounding a target nerve structure may also be quite different among different patients, and the neural response to stimulation may be markedly dissimilar, with an electrical stimulation pulse pattern, pulse width, frequency, and/or amplitude that is effective to reduce affect a body function one patient potentially imposing significant discomfort or pain on, or have limited effect for, another patient. Even in patients where implantation of a neurostimulation system provides effective treatment, frequent adjustments and changes to the stimulation protocol are often required before a suitable treatment program can be determined, often involving repeated office visits and significant discomfort for the patient before efficacy is achieved. While a number of complex and sophisticated lead structures and stimulation setting protocols have been implemented to seek to overcome these challenges, the variability in lead placement results, the clinician time to establish suitable stimulation signals, and the discomfort (and in cases the significant pain) that is imposed on the patient remain less than ideal. In addition, the lifetime and battery life of such devices is relatively short, such that implanted systems are routinely replaced every few years, which requires additional surgeries, patient discomfort, and significant costs to healthcare systems.

While rechargeable implanted devices have been investigated, the location and depth at which neurostimulation devices are implanted makes recharging of such devices difficult. For example, neurostimulation devices are typically implanted beneath a thin layer of muscle and fatty tissues in a lower back region such that conventional methods may utilize invasive techniques, such as recharging through a transcutaneous cable, or increased device size which may cause discomfort and limited mobility for the patient. Furthermore, given the location at which such devices are implanted—the lower back—attaching a recharging cable or device can be difficult, if not impossible, for a patient to perform without the aid of another person.

In view of these drawbacks associated with conventional systems, the tremendous benefits of these neural stimulation therapies have not yet been fully realized. Therefore, it would be desirable to provide improved methods, systems and devices for facilitating recharging of an implanted neurostimulation device. It would be particularly helpful to provide such systems and methods that recharge an implanted neurostimulation device in a non-invasive manner, while improving ease of use for the patient as well improved patient comfort and mobility during charging.

BRIEF SUMMARY OF THE INVENTION

Systems, devices and methods of the invention presented herein pertain to transcutaneous charging of an implanted medical device. In particular, the invention pertains to device and methods that facilitate positioning and alignment of a charging device and affixation of the charging device in the proper position and/or alignment to the patient.

In one aspect, a rechargeable medical implant system in accordance with embodiments of the invention includes: an implantable medical device having a rechargeable power source for powering the device while implanted within a patient and a wireless power receiving unit coupled with the rechargeable power source; a portable charging device having a wireless power transmitting unit configured to magnetically couple with the wireless power receiving unit of the implantable device so as to recharge the rechargeable power source; and a carrier removably coupleable with the charging device, the carrier having an adhesive surface for adhering to a skin surface of the patient, wherein the adhesive surface includes a biocompatible adhesive with sufficient adhesive strength to adhere to the patient's skin surface and support the carrier coupled with the charging device for at least a duration of time sufficient to recharge the implanted medical device. The wireless power transmitting unit of the charging device includes a charging coil configured for magnetically coupling with the wireless receiving unit when the charging device at least partially engages the patient's skin surface and is positioned at least partially over the implantable medical device, wherein the carrier secures the charging device substantially flat against the patient's skin.

In some embodiments, a carrier device in accordance with aspects of the invention includes one or more movable tabs on which an adhesive surface is disposed, each of the one or more tabs being movable between a first position and a second position when the carrier is coupled with the charging device placed against the patient's skin. In the first position, the one or more tabs are spaced away from the patient's skin to facilitate manual positioning of the charging device along the patient's skin. In the second position, the one or more tabs are urged against the patient's skin to facilitate secure attachment of the carrier to the patient's skin with the adhesive surface for the duration of charging.

In some embodiments, the carrier device includes one or more tabs extend circumferentially, at least partly, about the charging device when the carrier is coupled with the charging device so as to secure the charging device substantially flat against the patient's skin when the carrier is adhered to the skin of the patient. The carrier may include a frame to which one or more tabs are attached, wherein the frame defines a mounting interface at which the charging device is removably coupled. The mounting interface of the carrier is configured to allow manual rotation of the charging device relative to the carrier while releasably coupled with the carrier.

In one aspect, the carrier includes a mounting interface configured with a dimensional fit that allows rotation of the charging device when the charging device is subjected to a moment force and sufficient friction to maintain angular fixation of the charging device within the carrier when the charging device is static. In some embodiments, the charging device is defined by a circular or puck-shaped housing supporting and/or encasing the wireless power transmitting unit and associated charging coil at least partially within a protruding circular portion of the housing. The frame of the carrier comprises a circular ring and the mounting interface comprises a ridge along an inside edge of the circular ring that interfaces with an outer edge of the protruding portion of the charging device. The mounting can be configured to resiliently receive the protruding circular portion of the charging device within a snap-fit.

In some embodiments, the carrier device includes three or more tabs disposed circumferentially about a central frame of the device and extending laterally outward from the frame, each tab being deflectable between first and second positions. In one aspect, the tabs are formed of a material that is sufficiently stiff and flexible to resiliently invert (pass over center) between the first and second positions. The frame and the one or more tabs can be integrally formed of a polymeric material and may be disposable.

In one aspect, the carrier device includes a coupling interface that releasably couples to the charger device and has one or more movable tabs having adhesive portions for securely adhering to a skin of the patient, the adhesive portions being isolated from the charger device. In some embodiments, the adhesive portions are disposed on the one or more tabs so that the adhesive portions are not in contact with a surface of the charging device. Such a configuration is advantageous as it avoids accumulation of residual adhesive on the charger device, which is re-used over many charging sessions.

In another aspect, the charger device can be disposable, the adhesive portions providing secure attachment to the patient for at least a sufficient duration of time to charge the device. The carrier device can then be readily removed from the charger device and discarded or recycled after the charging session is complete. In some embodiments, the carrier device is provided to a patient with one or more liners disposed over the adhesive portions to preserve and protect the adhesive until ready for use. A single liner that extends over all adhesive portions can be used so that the charger device can be secured and the single liner removed thereby exposing all adhesive portions. In some embodiments, the patient is provided with multiple disposable carrier devices, such as a pack of carrier devices.

In another aspect, a carrier device for a portable charging device configured for transcutaneous charging of an neurostimulator device implanted in a patient is provided herein. Such carrier devices can defined by a semi-rigid or rigid frame configured for removably coupling with the charging device, wherein the frame includes an opening through which a portion of the charging device extends when the charging device is coupled with the frame; and one or more tabs attached to the frame and extending laterally outward from the opening of the frame, wherein the one or more tabs include an adhesive surface having a biocompatible adhesive with sufficient adhesive strength to adhere to a skin surface of the patient and support the carrier coupled with the charging device for a duration of time sufficient to recharge the implanted neurostimulator. Each of the one or more tabs is movable between a first position and a second position when the carrier is coupled with the charging device placed against the patient's skin, wherein in the first position, the one or more tabs are spaced away from the patient's skin to facilitate manual positioning of the charging device along the patient's skin and, in the second position, the one or more tabs are urged against the patient's skin to facilitate secure attachment of the carrier to the patient's skin with the adhesive surface for the duration of charging. Such carrier devices may include any of the features described in the systems above.

In some embodiments, the charging device carrier includes a frame defined by a circular ring having a circular opening dimensioned to fittingly received a circular protruding portion of the charging device having a charging coil therein. The carrier includes one or more tabs disposed circumferentially about the opening that extend laterally outward as to support and maintain the charging device substantially flat against the patient's skin when the charging device is coupled to the carrier and the tabs are adhered to the skin of the patient.

Methods of transcutaneously charging an implanted medical device in a patient in accordance with aspects of the invention are also provided herein. Such methods includes steps of: removably coupling a portable charging device having a housing and a charging coil disposed therein with a carrier having one or more tabs with a biocompatible adhesive surface, the one or more tabs being movable between a first position and a second position; non-invasively engaging a bottom surface of the charging device at least partially against a skin surface of the patient while mounted within the carrier with the one or more tabs in the first position spaced a distance away from the skin surface of the patient; positioning the charging device until it is at least partially positioned over or proximate the implanted medical device; and moving the one or more tabs from the first position to the second position so that the adhesive surface contacts and adheres to the skin of the patient sufficiently to support the charging device coupled with the carrier for a duration of time sufficient to charge the implanted device.

In some embodiments, positioning the charging device includes moving the charging device along the skin surface of the patient near the implanted device until the charging device outputs user feedback that indicates to the patient that the charging device is properly positioned. Typically, the first alert can be audible and/or haptic user feedback. The method may further include rotating the charging device relative to the carrier while the one or more tabs secure the carrier to the skin surface of the patient until the charging device is rotationally aligned with the implanted device, which may be indicated by user feedback, such as a second alert. In one aspect, each of engaging the bottom surface of the charging device with the skin of the patient, positioning the charging device, rotating the charging device relative the carrier, and moving the one or more tabs to the second position is performed with a single hand of the patient, thereby providing improved patient comfort and ease of use.

In some embodiments, the charge device carrier includes a belt. The belt can be formed of a breathable stretchable material and include a corresponding coupling feature on each opposing end adapted to releasably couple with each other to allow a patient to adjust the belt to a mid-section as desired. A circular aperture can be disposed in an intermediate portion of the belt. The circular aperture is dimensioned to fittingly receive a protruding circular portion of the portable charging device. A semi-rigid or rigid frame circumscribes the circular aperture and has a mounting interface adapted for removably coupling with the charging device so that the protruding circular portion of the charging device protrudes through the circular aperture and engages skin of the patient when the charging device is coupled to the belt worn on the mid-section of the patient. In some embodiments, the mounting interface is axisymmetric about a normal axis extending through a center of the circular aperture so as to allow the patient to manually rotate the charging device when coupled with the belt to a particular rotational alignment.

In some embodiments, methods of transcutaneously charging an implanted medical device in a patient include removably coupling a portable charging device having a housing and a charging coil within a carrier belt having a circular aperture so that the circular bottom portion protrudes through the aperture when coupled. A bottom surface of the charging device is non-invasively engaged with at least partially against a skin surface of the patient while mounted within the carrier belt. The charging device is positioned by the patient until at least partially positioned over or proximate the implanted medical device as indicated by a first audible and/or haptic signal from the charging device. The belt is adjusted by releasably coupling corresponding coupling features on opposite ends of the belt. The belt can be positioned before, during or after positioning of the charging device by the patient. The method can further include manually rotating the charging device while coupled within the belt until a second audible and/or haptic signal indicates an acceptable charging alignment for charging.

In one aspect, a method of transcutaneously charging an implanted medical device in a patient includes use of different indicators (e.g. audible and/or haptic alerts) to assist a patient in charging of the implanted medical device with a portable charging device. Such methods can include: placing a portable charger device on the patient to facilitate charging of an implanted neurostimulation within the patient; positioning the portable charger device until the charging device outputs a first indicator to the patient indicating that the charging device is proximate or suitably positioned over the implanted device for charging; adjusting a position of the portable charger device or an attachment device supporting the charger device in response to a second indicator output by the charging device indicating an interruption in charging; and removing the charging device after a third indication is output by the charging device indicating completion of charging. Typically, each of the first, second and third indicators is unique so as to be readily identifiable by the patient. Each of the first, second and third indicators can be an audible alert and/or a haptic alert. In some embodiments, the first alert is a sustained tone. The second indicator can be a periodic vibration and/or a series of short tones, such as three beeps and vibration repeated every few seconds. The third indicator can include a repeating series of short tones that is different from that of the second indicator, for example, a series of rising tones that repeats, to alert the patient that charging is complete so that the charging device can be removed.

In another aspect, a system in accordance with the invention can include an implantable medical device and a portable charging device having an indicator graphic for visually representing a target alignment of the charging device relative the implanted medical device. Such a system can include an implantable medical device having a rechargeable power source for powering the device while implanted within a patient and a wireless power receiving unit coupled with the rechargeable power source; and a portable charging device having a wireless power transmitting unit configured to magnetically couple with the wireless power receiving unit of the implantable device for recharging of the rechargeable power source. The portable charging device can include a planar surface for engaging a skin of the patient over the implanted medical device to facilitate charging. The indicator graphic can be provided on the planar surface and/or on the opposing outward facing surface and represent a target alignment of the charging device relative the implanted medical device to facilitate alignment of the charging device by the patient. The indicator can be a graphic that is the size and shape (e.g. outline) of the implanted medical device, which can serve as a visual prompt or reminder to the patient as to the desired alignment of the charging device relative the implanted medical device. The system can further include a carrier device for supporting the charging device in the desired alignment, such as in any of the embodiments described herein.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION OF THE INVENTION

Figure 1:
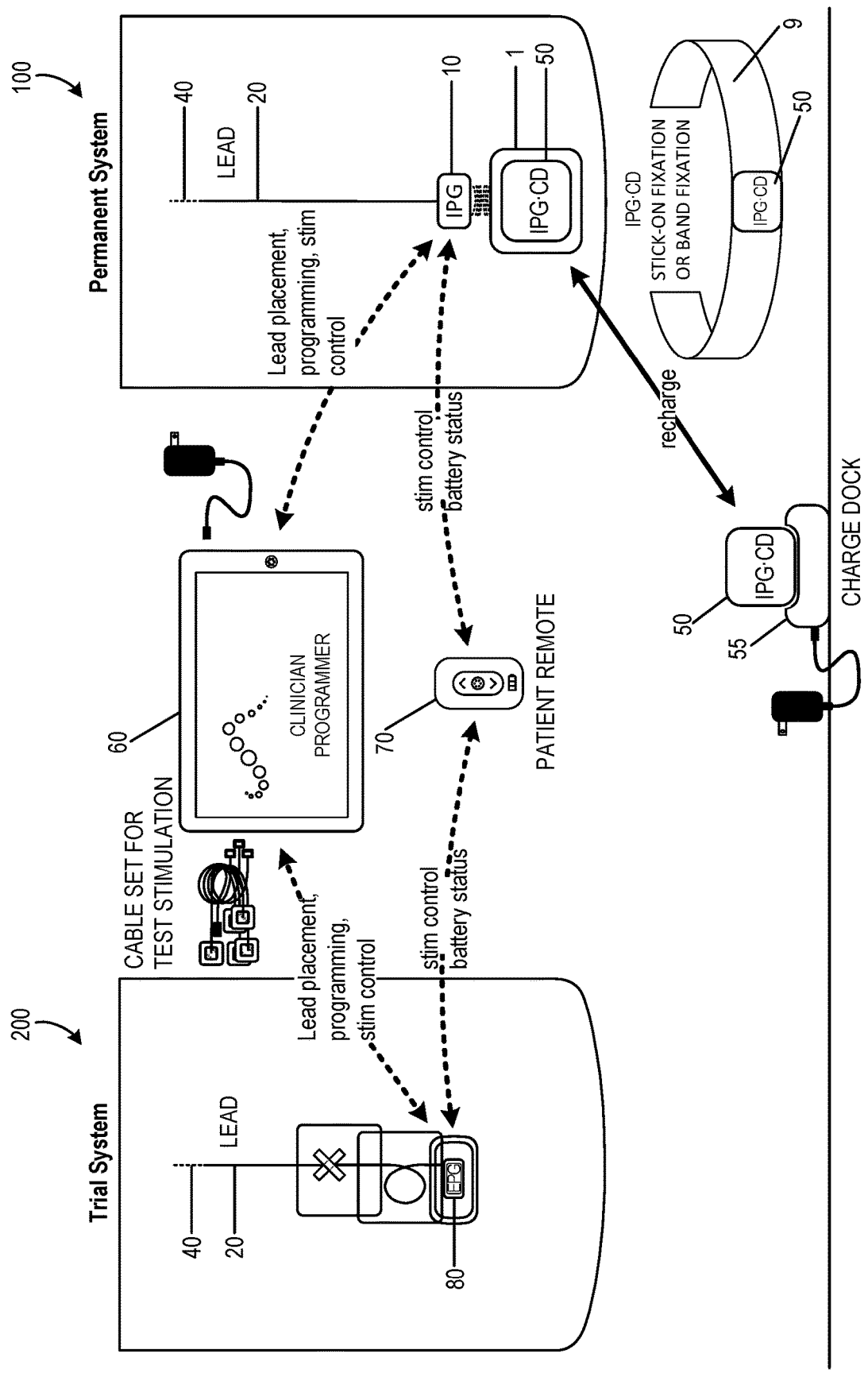
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment, implantation/placement and configuration of such treatment systems. In particular embodiments, the invention relates to sacral nerve stimulation treatment systems configured to treat bladder dysfunctions, including overactive bladder ("OAB"), as well as fecal dysfunctions and relieve symptoms associated therewith. In addition, the descriptions herein may also be used to treat other forms of urinary dysfunction and to treat fecal dysfunction, therefore, throughout the description it should be understood that what is described for OAB applies equally to other forms of urinary dysfunction and fecal dysfunction. It will be appreciated however that the present invention may also be utilized for any variety of neuromodulation uses, such as fecal dysfunction, the treatment of pain or other indications, such as movement or affective disorders, as will be appreciated by one of skill in the art.

I. Neurostimulation Indications

Neurostimulation (or neuromodulation as may be used interchangeably hereunder) treatment systems, such as any of those described herein, can be used to treat a variety of ailments and associated symptoms, such as acute pain disorders, movement disorders, affective disorders, as well as bladder and bowel related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 40 million Americans suffer from OAB. Of the adult population, about 16% of all men and women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of botulinum toxin (BTX), Percutaneous Tibial Nerve Stimulation (PTNS) and Sacral Nerve Stimulation (SNM). BTX is administered via a series of intradetrusor injections under cystoscopic guidance, but repeat injections of BTX are generally required every 4 to 12 months to maintain effect and BTX may undesirably result in urinary retention. A number or randomized controlled studies have shown some efficacy of BTX injections in OAB patients, but long-term safety and effectiveness of BTX for OAB is largely unknown.

PTNS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PTNS has been demonstrated in a few randomized-controlled studies, however, there is limited data on PTNS effectiveness beyond 3-years and PTNS is not recommended for patients seeking a cure for urge urinary incontinence (UUI) (e.g., 100% reduction in incontinence episodes) (EAU Guidelines).

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG). The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

A. Implantation of Sacral Neuromodulation System

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement, as described in Table 1 below. A temporary stimulation lead (a unipolar electrode) is then placed near the sacral nerve under local anesthesia. This procedure can be performed in an office setting without fluoroscopy. The temporary lead is then connected to an external pulse generator (EPG) taped onto the skin of the patient during the trial phase. The stimulation level can be adjusted to provide an optimal comfort level for the particular patient. The patient will monitor his or her voiding for 3 to 7 days to see if there is any symptom improvement. The advantage of the PNE is that it is an incision free procedure that can be performed in the physician's office using local anesthesia. The disadvantage is that the temporary lead is not securely anchored in place and has the propensity to migrate away from the nerve with physical activity and thereby cause failure of the therapy. If a patient fails this trial test, the physician may still recommend the staged trial as described below. If the PNE trial is positive, the temporary trial lead is removed and a permanent quadri-polar tined lead is implanted along with an IPG under general anesthesia. Other neuromodulation applications may have any number of electrodes and more than one lead as the therapy may require.

Figure 3A:
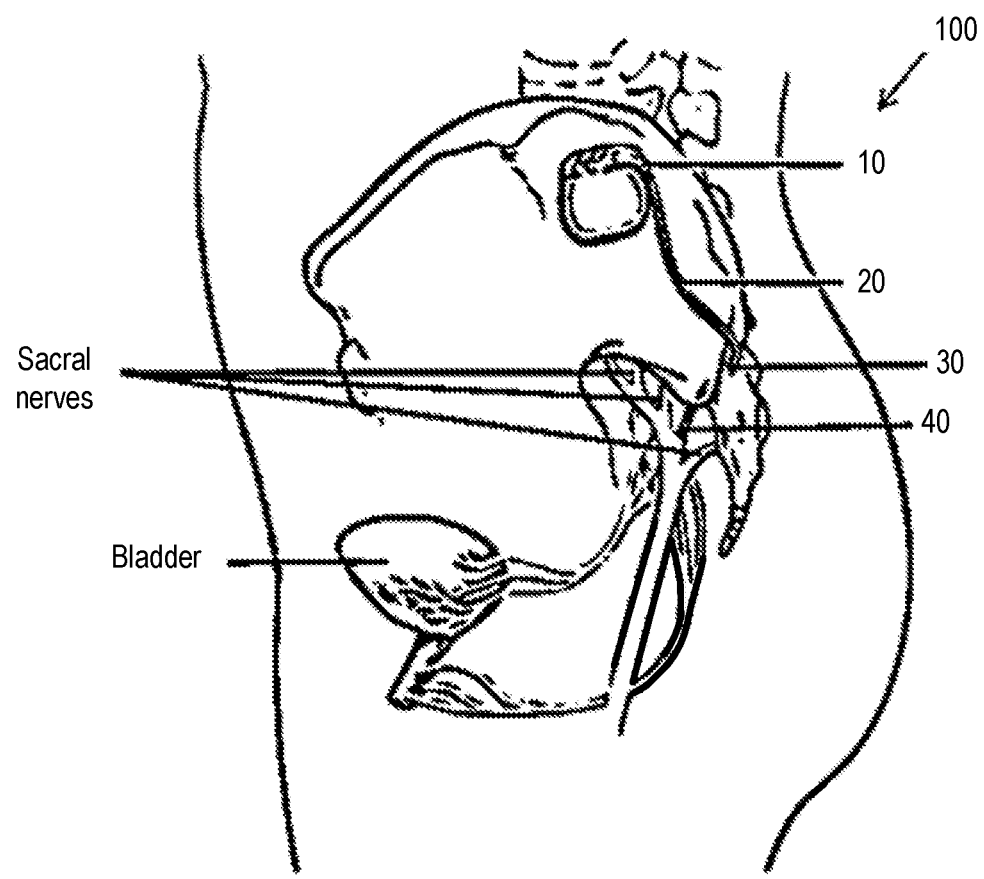
FIG. 3A shows an example of a fully implanted neurostimulation system in accordance with aspects of the invention.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIGS. 1 and 3A.

Table 1: Motor and Sensory Responses of SNM at Different Sacral Nerve Roots

TABLE 1

Motor and Sensory Responses of SNM at Different Sacral Nerve Roots

| | Response | | |
|---|---|---|---|
| Nerve Innervation | Pelvic Floor | Foot/calf/leg | Sensation |
| S2—Primary somatic contributor of pudendal nerve for external sphincter, leg, foot | "Clamp" * of anal sphincter | Leg/hip rotation, plantar flexion of entire foot, contraction of calf | Contraction of base of penis, vagina |
| S3—Virtually all pelvic autonomic functions and striated mucle (levetor ani) | "bellows" ** of perineum | Plantar flexion of great toe, occasionally other toes | Pulling in rectum, extending forward to scrotum or labia |
| S4—Pelvic autonomic and somatic; No leg pr foot | "bellows" ** | No lower extremity motor stimulation | Pulling in rectum only |

* Clamp: contraction of anal sphincter and, in males, retraction of base of penis. Move buttocks aside and look for anterior/posterior shortening of the perineal structures.
** Bellows: lifting and dropping of pelvic floor. Look for deepening and flattening of buttock groove In regard to measuring outcomes for SNM treatment of voiding dysfunction, the voiding dysfunction indications (e.g., urge incontinence, urgency-frequency, and non-obstructive urinary retention) are evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day. For FI patients, the outcome measures captured by the voiding diary include: number of leaking episodes per week, number of leaking days per week, and degree of urgency experienced before each leak.

The mechanism of action of SNM is multifactorial and impacts the neuro-axis at several different levels. In patients with OAB, it is believed that pelvic and/or pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pelvic and/or pudendal nerve afferents originating from the pelvic organs into the spinal cord. At the level of the spinal cord, these afferents may turn on voiding reflexes by suppressing exaggerated guarding reflexes, thus relieving symptoms of patients with urinary retention so normal voiding can be facilitated. In patients with fecal incontinence, it is hypothesized that SNM stimulates pelvic and/or pudendal afferent somatic fibers that inhibit colonic propulsive activity and activates the internal anal sphincter, which in turn improves the symptoms of fecal incontinence patients. The present invention relates to a system adapted to deliver neurostimulation to targeted nerve tissues in a manner that that results in partial or complete activation of the target nerve fibers, causes the augmentation or inhibition of neural activity in nerves, potentially the same or different than the stimulation target, that control the organs and structures associated with bladder and bowel function.

B. Positioning Neurostimulation Leads with EMG

While conventional sacral nerve stimulation approaches have shown efficacy in treatment of bladder and bowel related dysfunction, there exists a need to improve positioning of the neurostimulation leads and consistency between the trial and permanent implantation positions of the lead. Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (e.g., patient is under general anesthesia).

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, PNE may be done under local anesthesia, using a test needle to identify the appropriate sacral nerve(s) according to a subjective sensory response by the patient. Other testing procedures can involve a two-stage surgical procedure, where a quadripolar tined lead is implanted for a testing phase (phase 1) to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

In exemplary embodiments, determination of whether or not an implantable lead and neurostimulation electrode is located in a desired or correct location can be accomplished through use of electromyography ("EMG"), also known as surface electromyography. EMG, is a technique that uses an EMG system or module to evaluate and record electrical activity produced by muscles, producing a record called an electromyogram. EMG detects the electrical potential generated by muscle cells when those cells are electrically or neurologically activated. The signals can be analyzed to detect activation level or recruitment order. EMG can be performed through the skin surface of a patient, intramuscularly or through electrodes disposed within a patient near target muscles, or using a combination of external and internal structures. When a muscle or nerve is stimulated by an electrode, EMG can be used to determine if the related muscle is activated, (i.e. whether the muscle fully contracts, partially contracts, or does not contract) in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measureable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measureable muscular reaction can be a partial or a complete muscular contraction, including a response below the triggering of an observable motor response, such as those shown in Table 1, depending on the stimulation of the target muscle. In addition, by utilizing a trial system that allows the neurostimulation lead to remain implanted for use in the permanently implanted system, the efficacy and outcome of the permanently implanted system is more consistent with the results of the trial period, which moreover leads to improved patient outcomes. Moreover, the capability of the EMG systems described herein to quantitatively sense partial contraction can facilitate the use of positioning and/or programming stimulation levels below those appropriate for reliable subjective assessment by the patient. Hence, pain associated with electrode positioning and/or programming may optionally be reduced or eliminated by the use of sub-subjective EMG stimulation signals, with the programming and/or positioning of some embodiments relying substantially, largely, primarily, or even entirely on sub-subjective stimulation signals.

C. Example Neurostimulation Systems

FIG. 1 schematically illustrates an exemplary nerve stimulation system, which includes both a trial neurostimulation system 200 and a permanently implanted neurostimulation system 100, in accordance with aspects of the invention. The EPG 80 and IPG 10 are each compatible with and wirelessly communicate with a clinician programmer 60 and a patient remote 70, which are used in positioning and/or programming the trial neurostimulation system 200 and/or permanently implanted system 100 after a successful trial. As discussed above, the clinician programmer can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the clinician programmer 60 is used by a physician to adjust the settings of the EPG and/or IPG while the lead is implanted within the patient. The clinician programmer can be a tablet computer used by the clinician to program the IPG, or to control the EPG during the trial period. The clinician programmer can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the clinician programmer 60 has a control unit which can include a microprocessor and specialized computer-code instructions for implementing methods and systems for use by a physician in deploying the treatment system and setting up treatment parameters. The clinician programmer generally includes a user interface which can be a graphical user interface, an EMG module, electrical contacts such as an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the clinician programmer may be configured for coupling with an electrical ground or ground patch, an electrical pulse generator (e.g., an EPG or an IPG), or the like. As noted above, the clinician programmer can include a module with hardware and computer-code to execute EMG analysis, where the module can be a component of the control unit microprocessor, a pre-processing unit coupled to or in-line with the stimulation and/or sensory cables, or the like.

In some aspects, the clinician programmer is configured to operate in combination with an EPG when placing leads in a patient body. The clinician programmer can be electronically coupled to the EPG wirelessly during test simulation or through a specialized cable set, and . and allow the clinician programmer to configure, modify, or otherwise program the electrodes on the leads connected to the EPG.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2A:
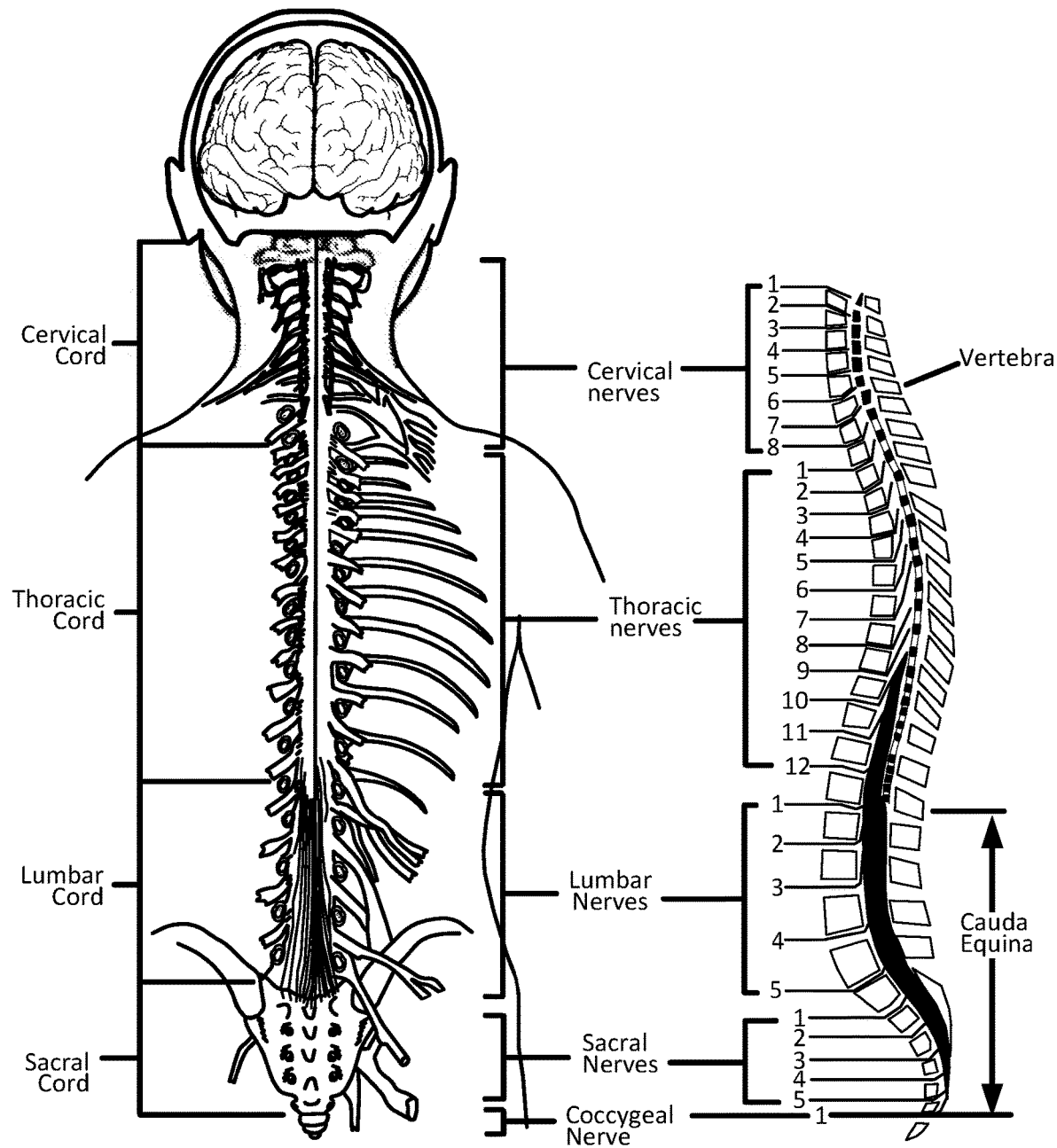
FIGS. 2A-2C show diagrams of the nerve structures along the spine, the lower back and sacrum region, which may be stimulated in accordance with aspects of the invention.
Figure 2B:
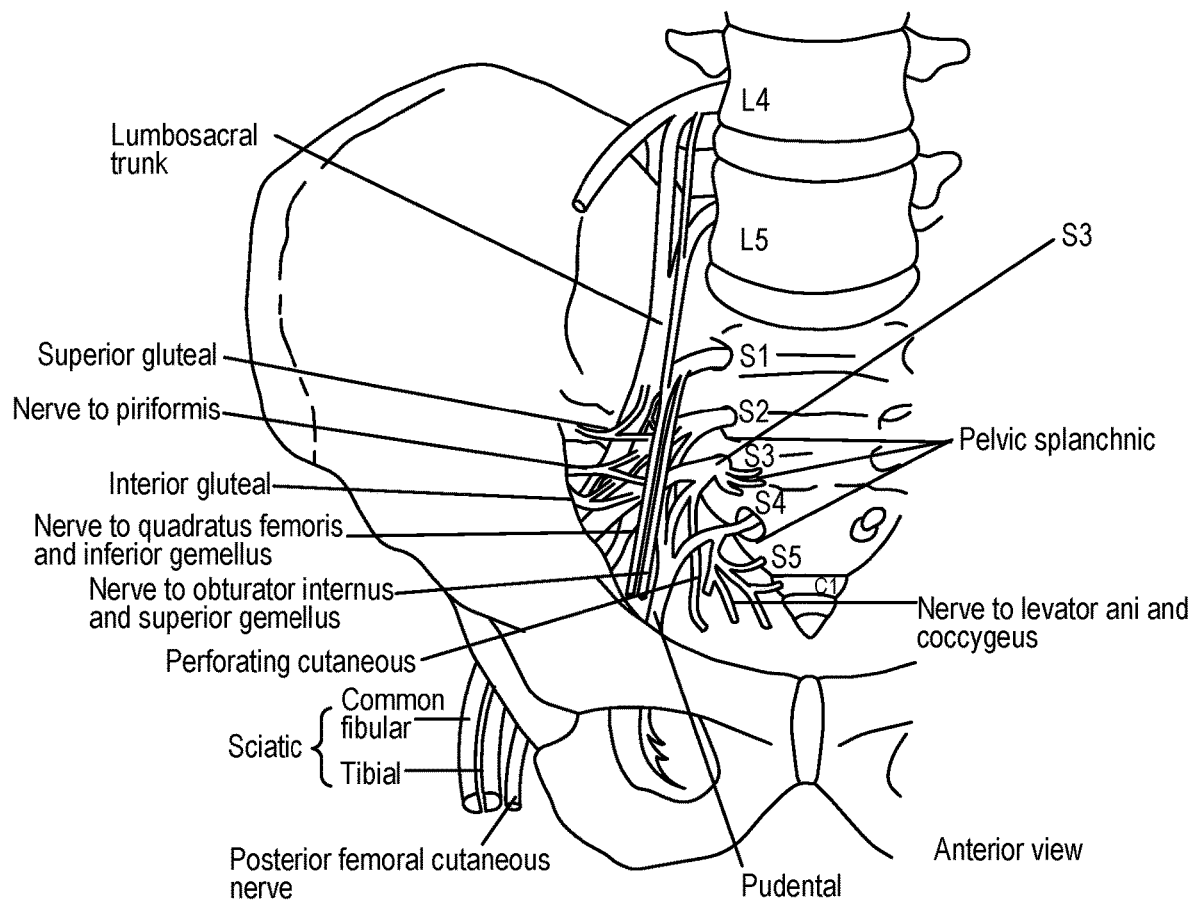
Figure 2C:
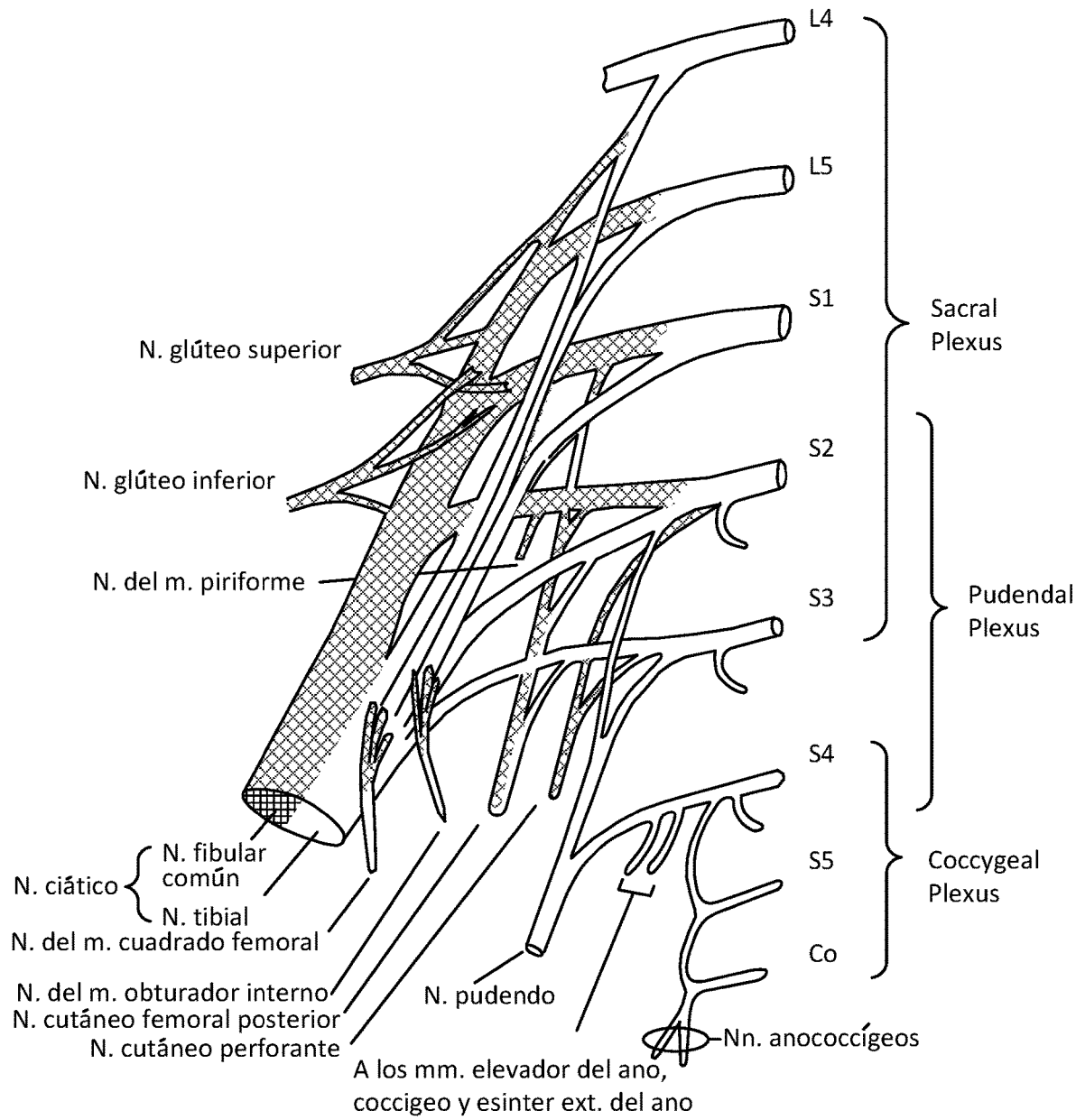

FIGS. 2A-2C show diagrams of various nerve structures of a patient, which may be used in neurostimulation treatments, in accordance with aspects of the invention. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, such as those in Table 1, either visually, through the use of EMG as described herein or both, the physician can determine whether the targeted nerve is being stimulated. While stimulation at a certain level may evoke robust muscle responses visible to the naked eye, stimulation at a lower level may still provide activation of the nerve associated with the targeted organ while evoking no corresponding muscle response or a response only visible with EMG. In some embodiments, this low level stimulation also does not cause any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder related dysfunction, and in particular OAB.

FIG. 3A schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, amplitude, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 3A, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

Figure 3B:
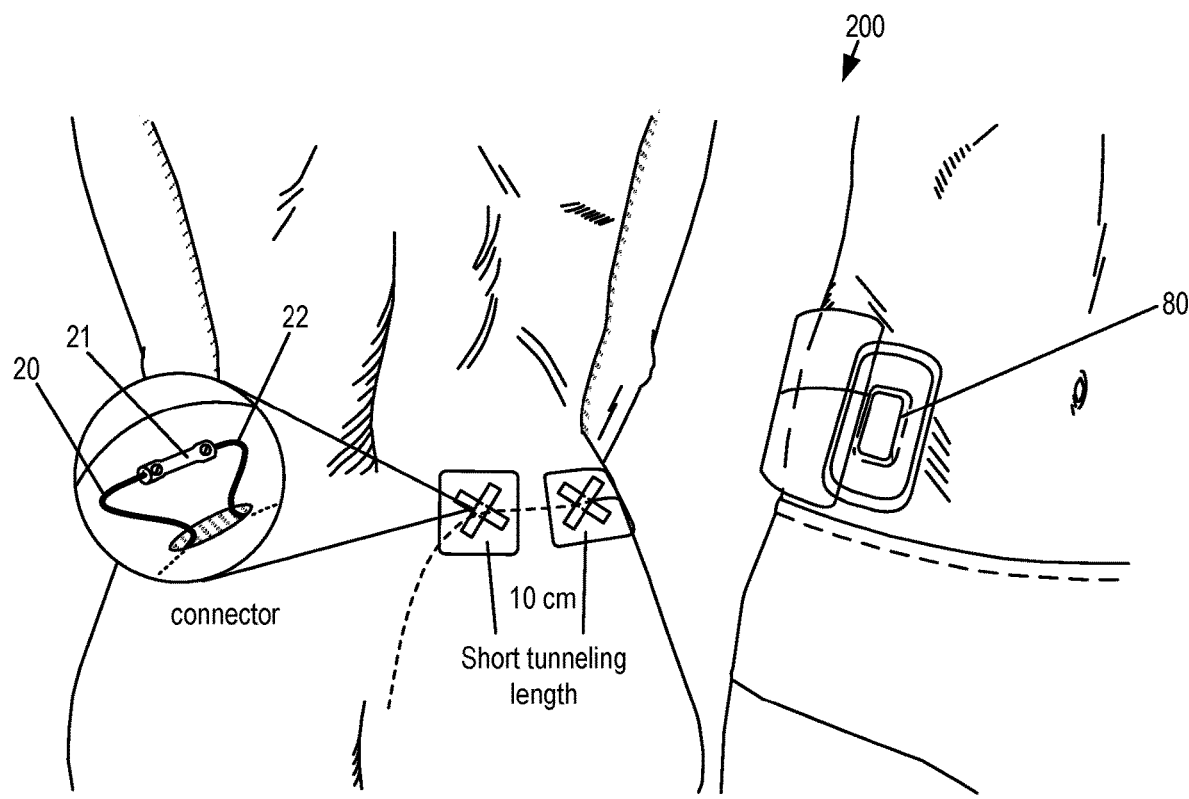
FIG. 3B shows an example of a neurostimulation system having a partly implanted stimulation lead and an external pulse generator adhered to the skin of the patient for use in a trial stimulation, in accordance with aspects of the invention.
Figure 3B:
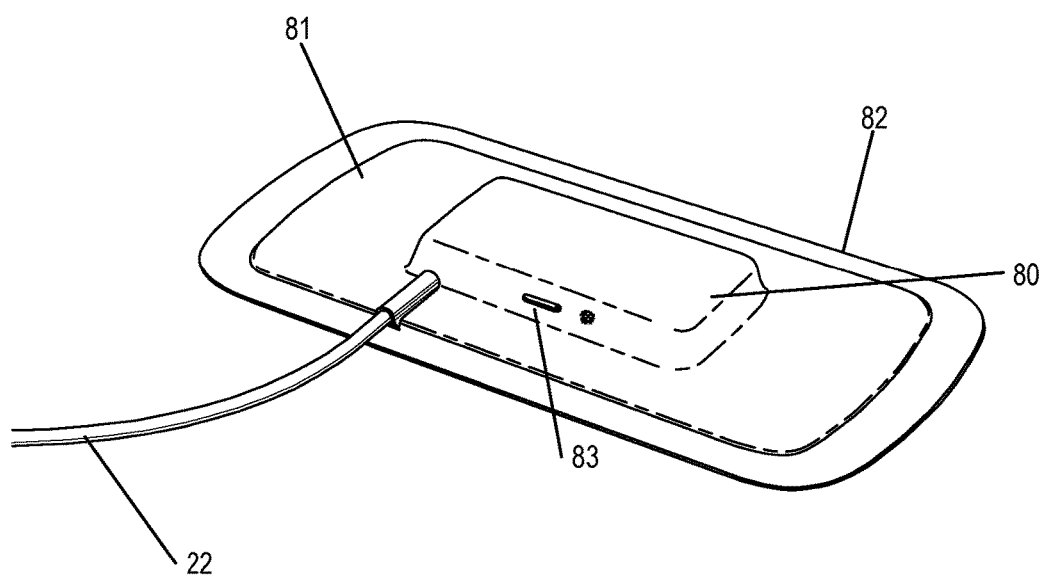

FIG. 3B shows a schematic illustration of a trial neurostimulation system 200 utilizing an EPG patch 81 adhered to the skin of a patient, particularly to the abdomen of a patient, the EPG 80 being encased within the patch. In one aspect, the lead is hardwired to the EPG, while in another the lead is removably coupled to the EPG through a port or aperture in the top surface of the flexible patch 81. Excess lead can be secured by an additional adherent patch. In one aspect, the EPG patch is disposable such that the lead can be disconnected and used in a permanently implanted system without removing the distal end of the lead from the target location. Alternatively, the entire system can be disposable and replaced with a permanent lead and IPG. When the lead of the trial system is implanted, an EMG obtained via the clinician programmer using one or more sensor patches can be used to ensure that the leads are placed at a location proximate to the target nerve or muscle, as discussed previously.

In some embodiments, the trial neurostimulation system utilizes an EPG 80 within an EPG patch 81 that is adhered to the skin of a patient and is coupled to the implanted neurostimulation lead 20 through a lead extension 22, which is coupled with the lead 20 through a connector 21. This extension and connector structure allows the lead to be extended so that the EPG patch can be placed on the abdomen and allows use of a lead having a length suitable for permanent implantation should the trial prove successful. This approach may utilize two percutaneous incisions, the connector provided in the first incision and the lead extensions extending through the second percutaneous incision, there being a short tunneling distance (e.g., about 10 cm) there between. This technique may also minimize movement of an implanted lead during conversion of the trial system to a permanently implanted system.

In one aspect, the EPG unit is wirelessly controlled by a patient remote and/or the clinician programmer in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The clinician programmer can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

As shown in the detailed view of FIG. 3B, the EPG 80 is encased within a flexible laminated patch 81, which include an aperture or port through which the EPG 80 is connected to the lead extension 22. The patch may further an "on/off" button 83 with a molded tactile detail to allow the patient to turn the EPG on and/or off through the outside surface of the adherent patch 81. The underside of the patch 81 is covered with a skin-compatible adhesive 82 for continuous adhesion to a patient for the duration of the trial period. For example, a breathable strip having skin-compatible adhesive 82 would allow the EPG 80 to remain attached to the patient continuously during the trial, which may last over a week, typically two weeks to four weeks, or even longer.

Figure 4:
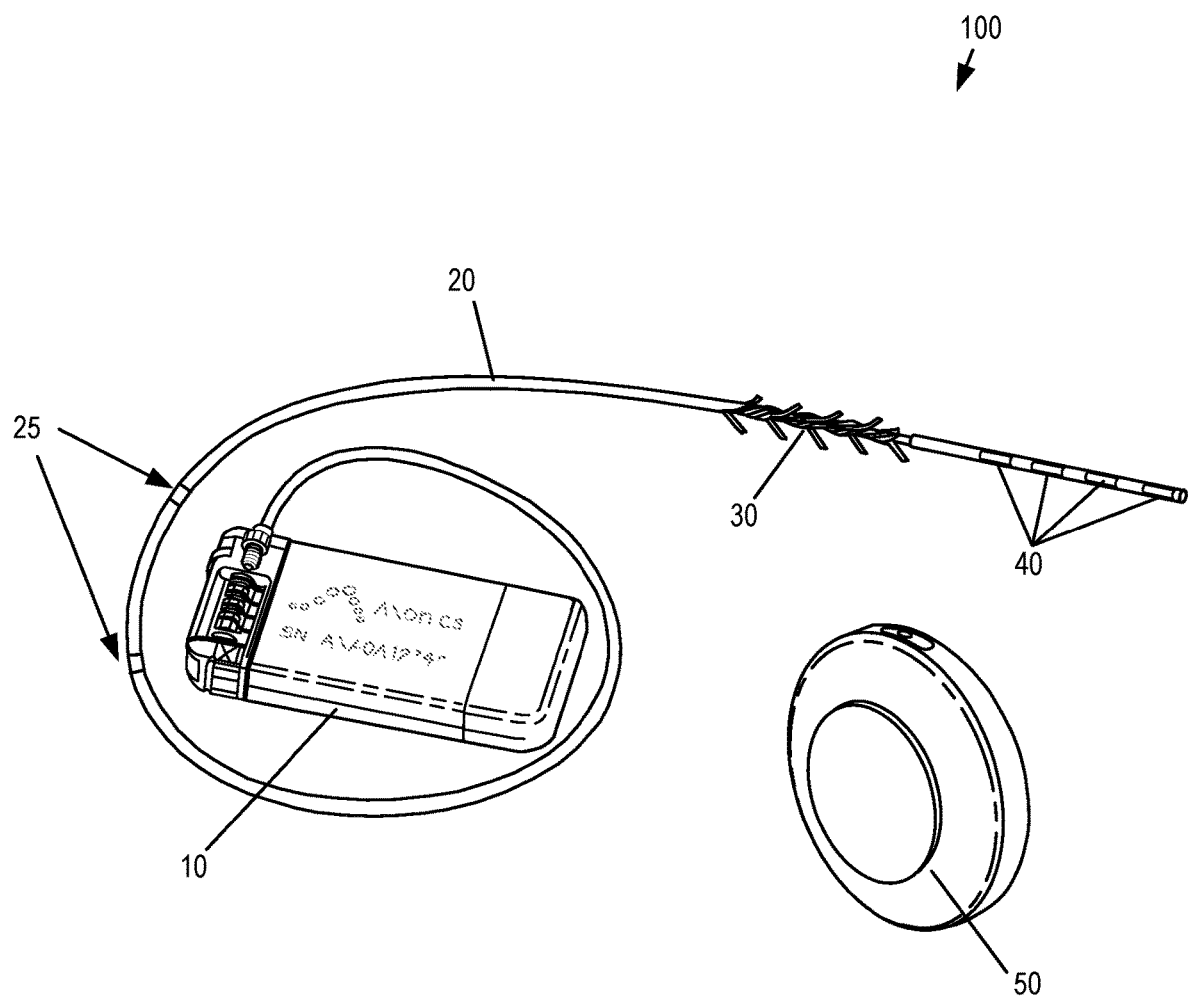
FIG. 4 shows an example of a neurostimulation system having an implantable stimulation lead, an implantable pulse generator, and an external charging device, in accordance with aspects of the invention.

FIG. 4 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes. In sacral nerve stimulation, the lead is typically implanted through the S3 foramen as described herein.

In one aspect, the IPG is rechargeable wirelessly through conductive coupling by use of a charging device 50 (CD), which is a portable device powered by a rechargeable battery to allow patient mobility while charging. The CD is used for transcutaneous charging of the IPG through RF induction. The CD can either be patched to the patient's skin with an affixation device, such as an adhesive carrier 1 or a belt 9. The CD may be charged by plugging the CD directly into an outlet or by placing the CD in a charging dock or station 55 that connects to an AC wall outlet or other power source.

The system may further include a patient remote 70 and clinician programmer 60, each configured to wirelessly communicate with the implanted IPG, or with the EPG during a trial, as shown in the schematic of the nerve stimulation system in FIG. 6. The clinician programmer 60 may be a tablet computer used by the clinician to program the IPG and the EPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off.

Figure 5A:
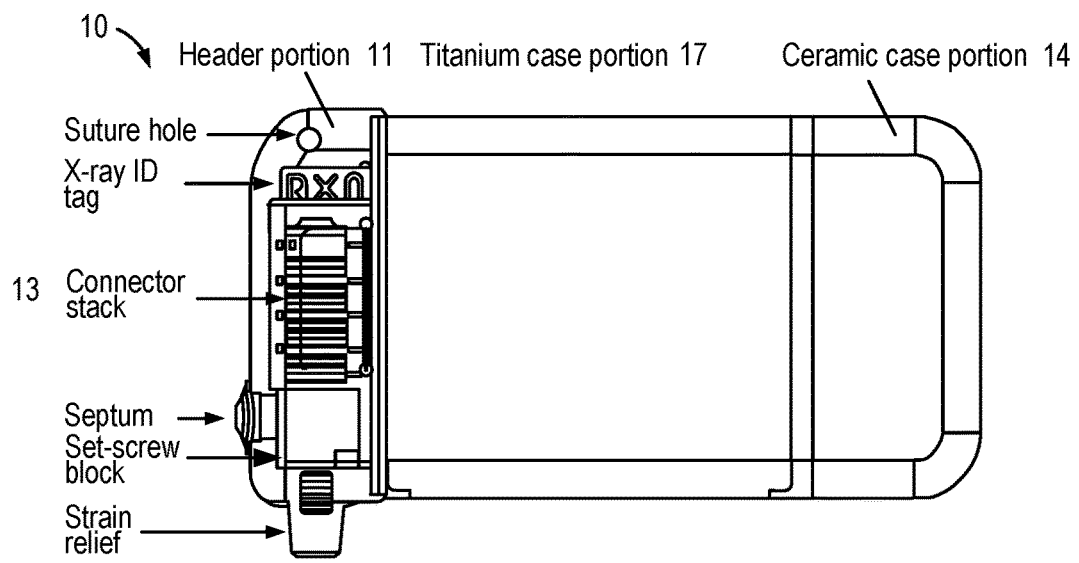
FIGS. 5A-5C show detail views of an implantable pulse generator and associated components for use in a neurostimulation system, in accordance with aspects of the invention.
Figure 5B:
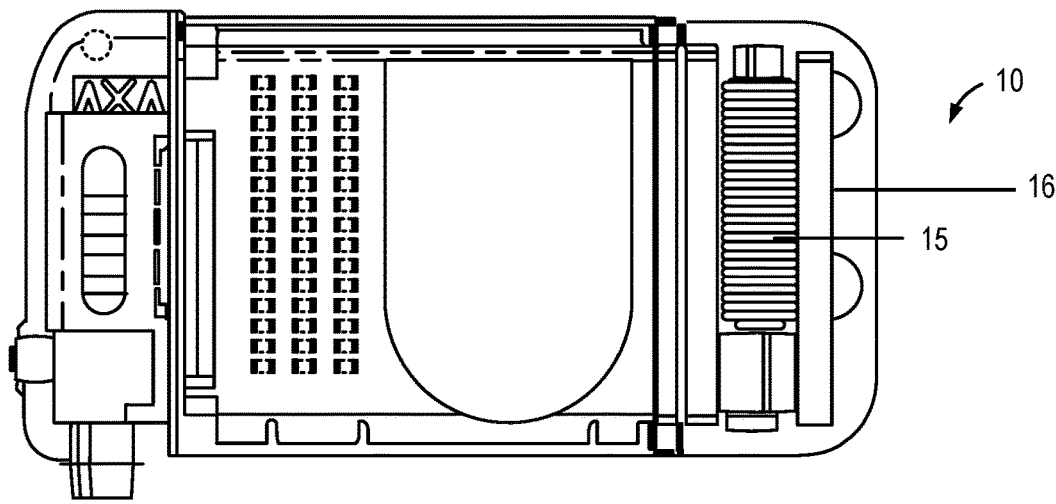
Figure 5C:
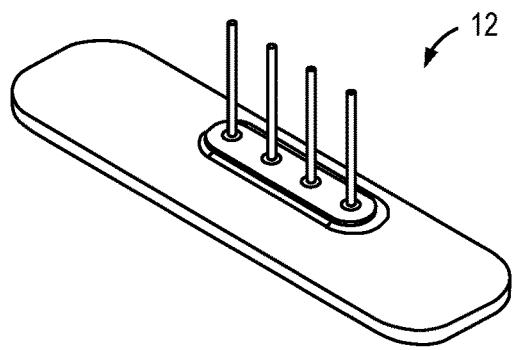

FIG. 5A-5C show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, one or more batteries, and typically includes a wireless charging unit.

One or more properties of the electrical pulses can be controlled via a controller of the IPG or EPG. In some embodiments, these properties can include, for example, the frequency, strength, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 10 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 µs to 500 µs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG may include a header portion 11 at one end and a ceramic portion 14 at the opposite end. The header portion 11 houses a feed through assembly 12 and connector stack 13, while the ceramic case portion 14 houses an antenna assembly 16 to facilitate wireless communication with the clinician program, the patient remote, and/or a charging coil to facilitate wireless charging with the CD. The remainder of the IPG is covered with a titanium case portion 17, which encases the printed circuit board, memory and controller components that facilitate the electrical pulse programs described above. In the example shown in FIG. 5C, the header portion of the IPG includes a four-pin feed-through assembly 12 that couples with the connector stack 13 in which the proximal end of the lead is coupled. The four pins correspond to the four electrodes of the neurostimulation lead. In some embodiments, a Balseal® connector block is electrically connected to four platinum/iridium alloy feed-through pins which are brazed to an alumina ceramic insulator plate along with a titanium alloy flange. This feed-through assembly is laser seam welded to a titanium-ceramic brazed case to form a complete hermetic housing for the electronics. The number of header electrical contacts is a function of the number of electrodes and leads used for any particular system configuration.

In some embodiments, such as that shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. It will be appreciated, however, that other ceramics or other suitable materials may be used for construction of the IPG.

In one aspect, utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and clinician programmer. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time.

In another aspect, the ferrite core is part of the charging coil assembly 15, shown in FIG. 5B, which is positioned inside the ceramic case 14. The ferrite core concentrates the magnetic field flux through the ceramic case as opposed to the metallic case portion 17. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. This configuration also allows the IPG to be effectively charged at depth of 3 cm with the CD, when positioned on a skin surface of the patient near the IPG and reduces re-charging time.

FIG. 6 shows a setup for a test stimulation and EMG sensing using a clinician programmer 60. As discussed above, the clinician programmer 60 is a tablet computer with software that runs on a standard operating system. The clinician programmer 60 includes a communication module, a stimulation module and an EMG sensing module. The communication module communicates with the IPG and/or EPG in the medical implant communication service frequency band for programming the IPG and/or EPG.

In order to confirm correct lead placement, it is desirable for the physician to confirm that the patient has both adequate motor and sensory responses before transitioning the patient into the staged trial phase or implanting the permanent IPG. However, sensory response is a subjective evaluation and may not always be available, such as when the patient is under general anesthesia. Experiments have shown that demonstrating appropriate motor responses is advantageous for accurate placement, even if sensory responses are available. As discussed above, EMG is a tool which records electrical activity of skeletal muscles. This sensing feature provides an objective criterion for the clinician to determine if the sacral nerve stimulation results in adequate motor response rather than relying solely on subjective sensory criteria. EMG can be used not only to verify optimal lead position during lead placement, but also to provide a standardized and more accurate approach to determine electrode thresholds, which in turn provides quantitative information supporting electrode selection for programming. Using EMG to verify activation of motor responses can further improve the lead placement performance of less experienced operators and allow such physicians to perform lead placement with confidence and greater accuracy.

In one aspect, the system is configured to have EMG sensing capability during re-programming, which can be particularly valuable. Stimulation levels during re-programming are typically low to avoid patient discomfort which often results in difficult generation of motor responses. Involuntary muscle movement while the patient is awake may also cause noise that is difficult for the physician to differentiate. In contrast to conventional approaches, EMG allows the clinician to detect motor responses at very low stimulation levels (e.g., sub-threshold), and help them distinguish a motor response originated by sacral nerve stimulation from involuntary muscle movement.

Referring to FIG. 6, several cable sets are connected to the clinician programmer. The stimulation cable set consists of one stimulation mini-clip 3 and one ground patch 5. It is used with a foramen needle 1 to locate the sacral nerve and verify the integrity of the nerve via test stimulation. Another stimulation cable set with four stimulation channels 2 is used to verify the lead position with a tined stimulation lead 20 during the staged trial. Both cable sets are sterilizable as they will be in the sterile field. A total of five over-the-shelf sensing electrode patches 4 (e.g., two sensing electrode pairs for each sensing spot and one common ground patch) are provided for EMG sensing at two different muscle groups (e.g., perineal musculature and big toe) simultaneously during the lead placement procedure. This provides the clinician with a convenient all-in-one setup via the EMG integrated clinician programmer. Typically, only one electrode set (e.g., two sensing electrodes and one ground patch) is needed for detecting an EMG signal on the big toe during an initial electrode configuration and/or re-programming session. Typically, these over-the-shelf EMG electrodes are also provided sterile though not all cables are required to be connected to the sterile field. The clinician programmer 60 allows the clinician to read the impedance of each electrode contact whenever the lead is connected to an EPG, an IPG or a clinician programmer to ensure reliable connection is made and the lead is intact. The clinician programmer 60 is also able to save and display previous (e.g., up to the last four) programs that were used by a patient to help facilitate re-programming. In some embodiments, the clinician programmer 60 further includes a USB port for saving reports to a USB drive and a charging port. The clinician programmer may also include physical on/off buttons to turn the clinician programmer on and off and/or to turn stimulation on and off.

III. Charging of Fully Implanted Neurostimulation Systems

In one aspect, a neurostimulation system in accordance with the present invention is fully implantable and powered with a rechargeable battery that allows the system to provide therapy over the lifetime of the device with only periodic transcutaneous charging by an external CD. This feature increases the useful life of the neurostimulation system as compared to conventional neurostimulation systems that utilize a non-rechargeable batteries which must be surgically removed and replaced every three to four years. This conventional approach to fully implanted neurostimulation systems clearly results in significant discomfort and inconvenience for the patient. In addition, many patients may be reluctant to receive a therapy that requires periodic surgical intervention every few years. In contrast, a neurostimulation system utilizing transcutaneous charging in accordance with the principles described herein allows such a system to function for 10 years or more without invasive interventions to replace a battery, thereby improving patient comfort and acceptance of implanted neurostimulation therapies.

In one aspect, the systems and methods provide transcutaneous charging of implanted devices by wireless charging that uses an electromagnetic field to transfer energy between two objects. This approach uses a charging station or device that sends energy through a magnetic or inductive coupling to an energy receiving unit of the implanted device, which then uses that energy to charge a battery in the implanted device. Such charging methods typically use an external device with a charging coil that creates an alternating electromagnetic field from within the charging unit, and a second coil in the implanted device in which an electromagnetic field is induced, which the implanted device then converts back into electrical current to charge the battery. The coils must generally be in close proximity to form an electrical transformer and maintained in close proximity for a duration of time sufficient to fully charge the battery. In many conventional devices, the coil configurations are such that the coils must be placed in close proximity, typically less than a few centimeters. While wireless charging at greater distances can be achieved through various other approaches, such as resonant inductive coupling, these approaches may require precise alignment between coils, while other approaches may require coils of increased size and/or high powered charging. Wireless charging can be further understood by reference to U.S. Pat. No. 6,972,543, entitled "Series resonant inductive charging circuit," which is incorporated herein by reference for all purposes.

The above noted aspects of wireless charging present substantial challenges to charging of implanted medical devices, since it is desirable for such devices to be of reduced size and weight, as well as to minimize exposure of the patient to high-powered charging stations. These aspects of wireless charging are particularly challenging in terms of implanted neurostimulation devices, which are typically implanted at a greater depths, such as a depth of about 3 cm, beneath a thin layer of muscle and/or fatty tissues in a lower back of the patient, where the patient cannot readily access or observe the placement and/or alignment of an external charging device. Given these challenges associated with wireless charging of implanted neurostimulation devices, conventional neurostimulation devices have utilized non-rechargeable batteries with life-times of about three to four years. While this approach avoids the above noted drawbacks, it is also subjects the patients to periodic invasive surgical procedures every time the battery needs to be replaced.

In one aspect, the system and charging methods of the present invention overcome these challenges associated with wireless charging due in part to the unique construction of the wireless receiving unit of the neurostimulation device and external CD, and also by use of certain features that improve positioning and alignment of the external CD with the implanted device to allow for more robust, consistent charging of the implanted device. In addition, the features described herein allow a patient to achieve that precise positioning and alignment with relative ease, without the aid of a caretaker or medical personnel. Furthermore, the above objectives are provided while still allowing for an implanted neurostimulation device of reduced size and weight and while maintaining patient mobility by use of a portable external charging device that remains attached to the patient during charging.

Figure 7A:
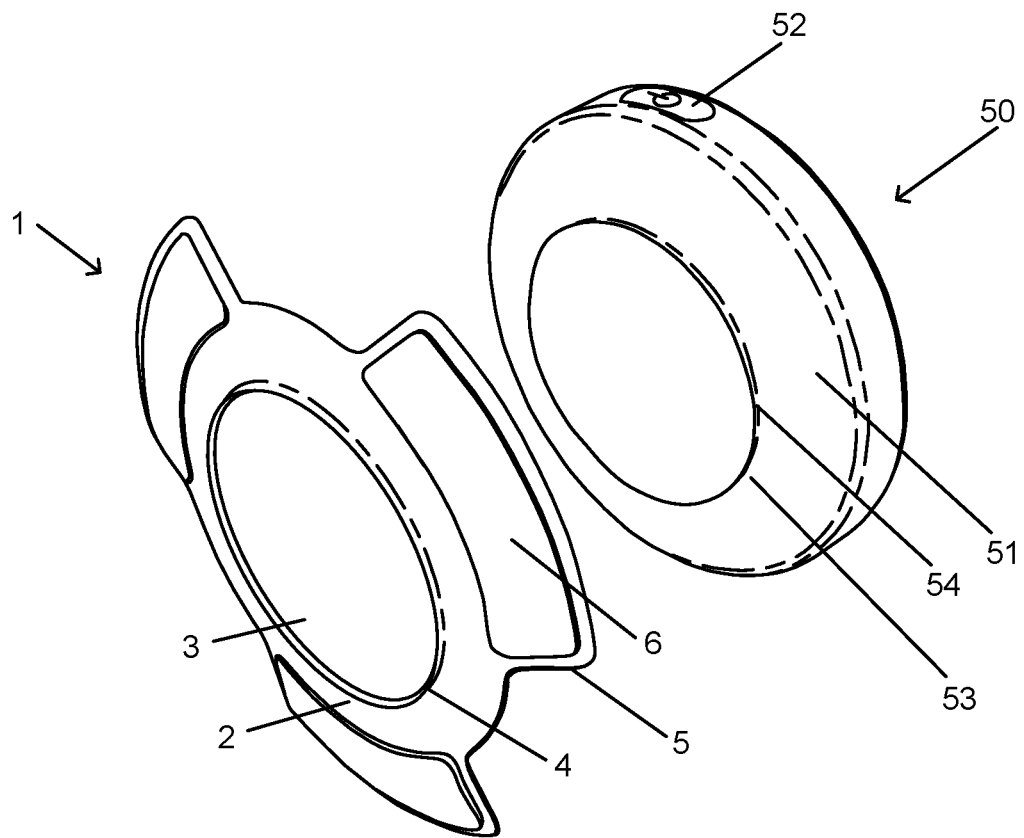
FIG. 7A shows an affixation device comprising an adhesive carrier adapted for use with a portable charging device, in accordance with aspects of the invention.
Figure 7B:
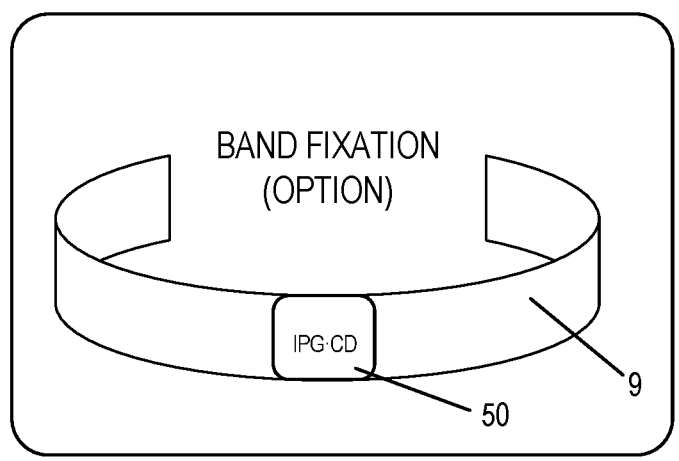
FIG. 7B shows another affixation device comprising a belt, in accordance with aspects of the invention.
Figure 7C:
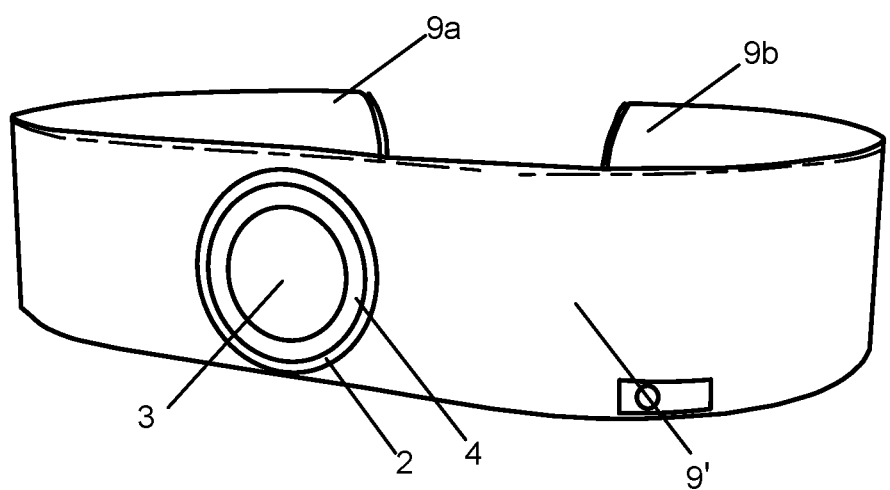
FIG. 7C shows another affixation device comprising a belt, in accordance with aspects of the invention.

In one aspect, the systems and methods described herein allow for transcutaneous charging of a fully implanted neurostimulation device by a portable external charging device adhered to the patient with an affixation device for a duration of time, typically less than a few hours, such as within two hours or less. In one aspect, the attachment device is adapted to allow placement of the external CD by the patient in a position and/or alignment suitable for wireless charging and to maintain that position and/or alignment for the duration of charging. Examples of such attachment devices are shown in FIGS. 7A-7C and described further below.

A. Implant Battery Charging Protocol

In some embodiments, the IPG of the neurostimulation system includes a charging coil adapted to capture energy necessary to recharge the internal battery. The battery voltage is measured through an Analog to Digital (A/D) converter of the IPG and is also monitored by the battery monitor during charging. The battery monitor compares the battery voltage with a voltage reference. Based on the battery monitor outputs, the current charger inside the implant is controlled accordingly. When the battery voltage is above 3.0V, it is in the normal charging mode. The charging current is set to the default value of ~25 mA (C/2). Charging will stop when the battery voltage reaches 4.05V to prevent over-charge. To charge up a battery with battery voltage between 2.5V and 3.0V, a smaller charging current (~2.5V) will be used until it reaches 3.0V where the battery goes into the normal charging mode. In some embodiments, the IPG charging circuitry is designed in a such way that no recharging is possible when the battery voltage is below 2.5V, to avoid potential thermal runaway causing rapid temperature increase of the battery, which is unlikely though due to the low capacity of the over-discharged battery. Field testing has demonstrated that such a battery can be safely recharged from a very low voltage state (0.1V). The battery voltage dropping below 2.5V is a very rare occurrence, because the IPG will be forced into a hibernation mode when the battery voltage drops below 3.0V during which the battery could only be drained by a tiny leakage current such that it would take more than one year for the battery voltage to drop below 2.5V from 3.0V. In some embodiments, the capacity of the implant battery is 50 mAh such that at nominal stimulation settings for OAB, the IPG lasts approximately two weeks before needing recharge.

In some embodiments, the external CD is a mobile puck-shaped device that is configured to provide wireless and transcutaneous recharging of the implanted IPG while maintained at a suitable position and/or alignment on the patient. The CD includes a microcontroller which handles control of charging and communication with the IPG. The CD also includes a battery, which can be recharged in a charging station or by coupling directly to a power source, which allows for charging while the patient is mobile. The CD is shaped and dimensioned to fit comfortably in a hand of the patient to facilitate placement of the CD on the patient for recharging, as well as to allow ready handling of the CD by the patient. In some embodiments, the CD includes a temperature sensor to ensure that the charger will never overheat. The charger monitors the battery charging status and automatically shuts itself off when the implant battery is fully charged.

In one aspect, the CD is a portable device having an enlarged upper portion and a protruding circular portion on a underside thereof. The enlarged upper portion, which typically includes the rechargeable battery and associated electronics and microcontroller, is dimensioned so as to be easily held by a user to facilitate handling and positioning of the CD by the patient. The protruding circular portion that houses the charging coil and includes a substantially planar surface for engaging the skin of the patient over the implanted IPG. While the CD is depicted as a puck-shaped device it is appreciated that the CD can be defined in various other shapes while still providing certain features of the various aspects described herein.

Figure 6A:
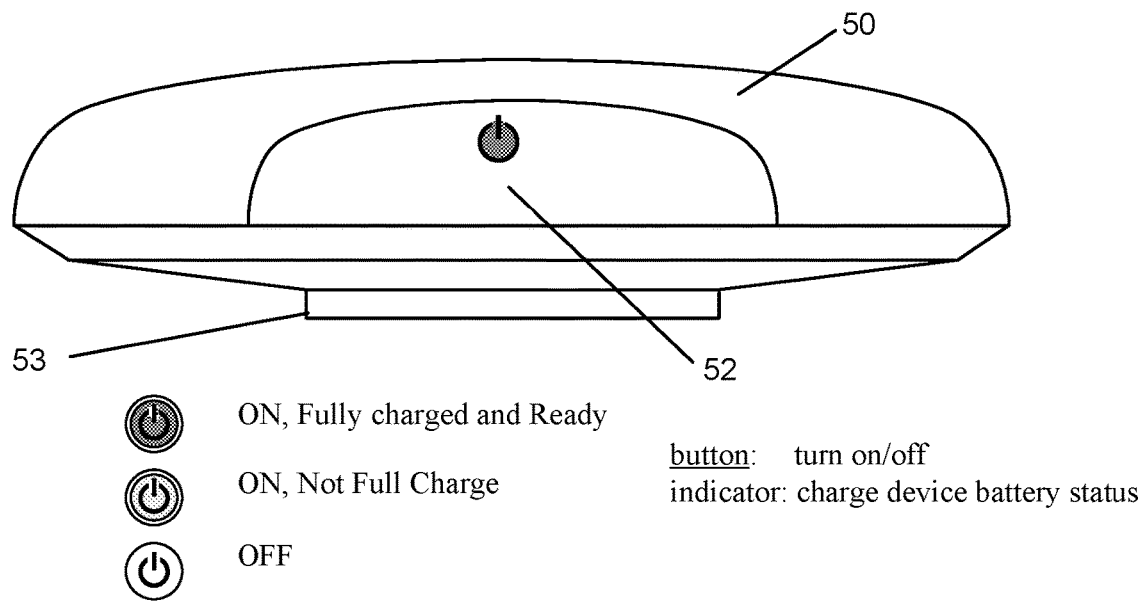
FIG. 6A shows a charging device configured for transcutaneous, wireless charging of an implanted neurostimulation device, in accordance with aspects of the invention.

FIG. 6A shows an example of an external, portable CD 50 in accordance with the aspect described above. The CD includes a puck-shaped upper portion that contains a rechargeable battery that can support at least 2 hours of continuous charging. This portion also includes an on/off button with an indicator light 52 indicates the charger battery status. Various differing colors or blinking can be used to indicate differing states. For example, a green light indicates that the charger battery is at a good charging state and should provide a full charge for a depleted IPG battery (e.g. up to 2 hours of charging); an amber light indicates that the charger battery has energy to provide limited amount of charging but may not be enough to fully charge a depleted IPG battery. A flashing amber light indicates that the CD has insufficient charge for even a partial charge to the IPG. The indicator is flashing green while the CD is being charged. The indicator illuminates only while the CD is on; the indicator is OFF when the CD is OFF. The circular portion 53 at bottom protrudes outwards so that the charging coil can be in closer proximity to the IPG to facilitate charging at greater depth, for example depths greater than 2 cm, typically up to depths of about 3 cm.

Figure 6B:
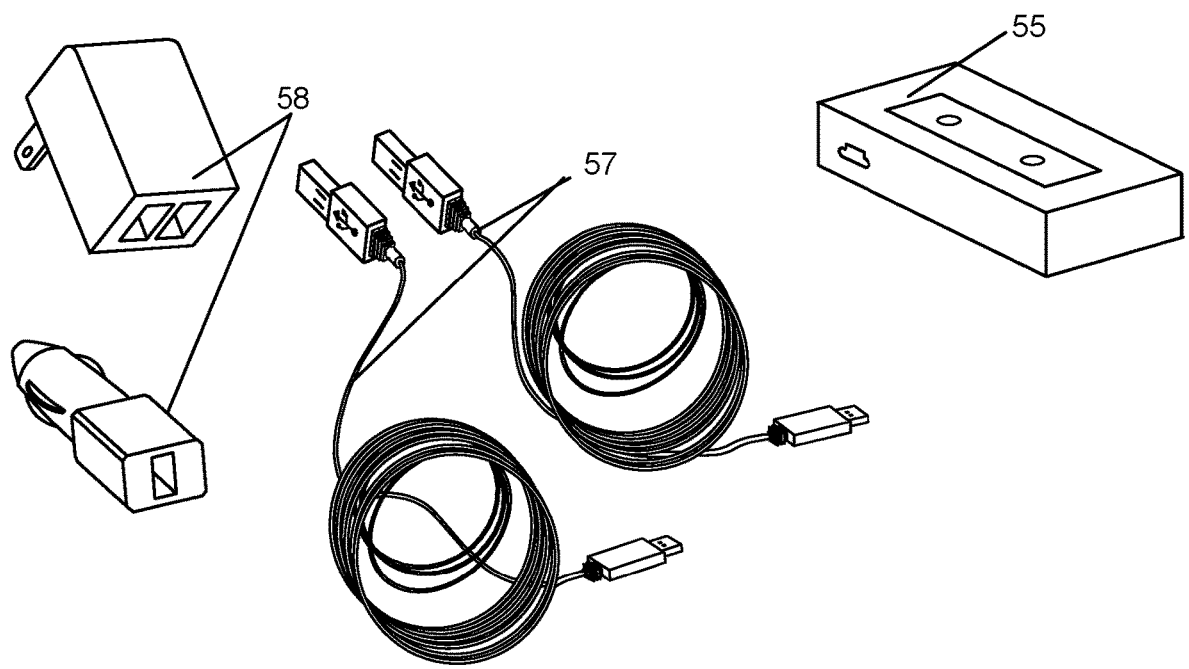
FIG. 6B shows accessories for charging a portable charging device, in accordance with aspects of the invention.

The CD may be charged by multiple options, such as those in FIG. 6B, which show a designated charging station 55, USB power cables 57, and may utilize USB power adapters 58 to for use with a wall outlet or a power outlet in a car.

Figure 6C:
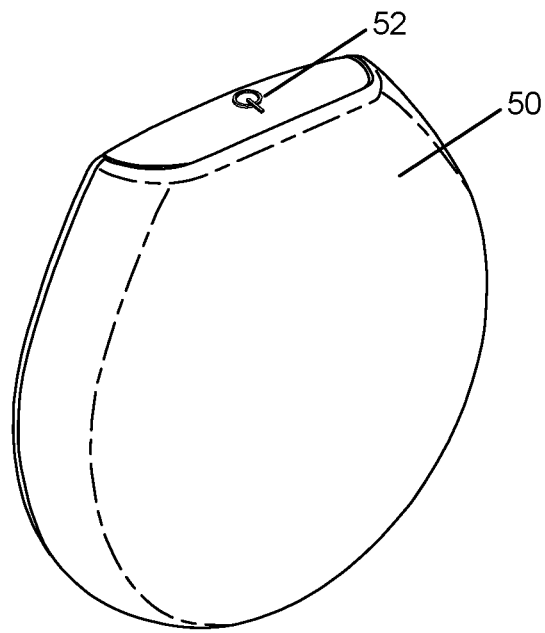
FIGS. 6C-6D shows another portable charging device and an associated docking station for charging the device, respectively, in accordance with aspects of the invention.
Figure 6D:
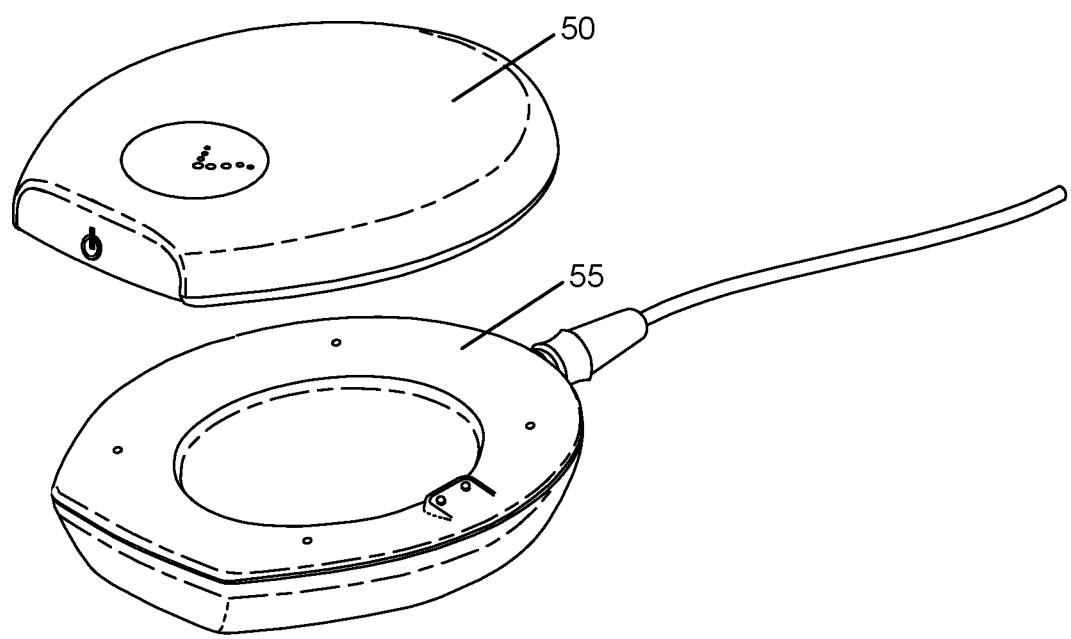

FIG. 6C shows another example CD 50 that includes a puck-shaped upper portion having an indicator light 52 and a protruding circular bottom portion (not shown). The upper portion, in this embodiment, includes a flattened side, which can facilitate handling by the patient and rotational orientation, as described further below. FIG. 6D shows a charging station 55 that utilizes a circular depression for receiving the protruding circular bottom portion of CD 50 to facilitate charging through the charging coil housed therein.

In some embodiments, to get the recharging started, the patient needs to move the CD over the implanted IPG. The CD provides audio feedback to assist the patient in finding the IPG. An audio transducer audibly indicates when the IPG is near the charging coil to the IPG. The CD emits three short beeps when the CD is close to the IPG (enough to be detectable) yet not within the charging zone, and a long beep to indicate the CD is in the IPG charging zone.

Optionally, a patient will then rotate the CD to achieve better angular alignment. A haptic feedback is provided when optimal angular alignment is achieved between the CD and IPG. An audio tone signals that the IPG is now being charged by the CD. In addition, a periodic green flashing light on the CD indicates the charging is currently on-going. If optimal alignment is not achieved within 15 seconds, but the charging field is strong enough to charge the implant battery, the charging process will continue, and the audio will turn off. If the charger moves during charging and charging field is lost completely, the CD will emit 3 short beeps while in range yet not in the IPG charging zone. This alerts the user that the CD is off target and needs to be re-located over the IPG. When charging is complete, the CD provides a user indication that charging is complete and powers off. For example, the CD can output a unique series of audio tones (e.g. three short beeps) that indicate the end of charging and the flashing green light will be off. In some embodiments, a watchdog timer is used to verify that the microcontroller is operational. In the event of program malfunction, the microcontroller will enter a safe state that either powers down the coil or turns off the coil drive.

By utilizing the devices and charging methods described herein, the IPG can be recharged at greater depths, such as about 3 cm. Having a deep charging depth allows for improved patient comfort during charging as it allows the implant to be placed in a desirable location within tissues while still allowing for transcutaneous wireless charging with a portable CD. To efficiently recharge the described, however, a precise position and/or alignment of the CD must be achieved and reasonably maintained for a duration of time sufficient to complete charging of the IPG battery. This can be accomplished by use of various affixation methods and devices adapted for use with the CD, such as those shown and described below.

B. Example Affixation Devices

In one aspect, the carrier device includes a frame releasably coupleable with the CD and having multiple outwardly extending tabs with a pressure sensitive adhesive suitable for adhesively securing the CD to the skin of the patient. The frame is configured to allow the CD to contact a skin of the patient directly over the implanted IPG so as to minimize distance between the CD and implanted IPG.

FIG. 7A shows such a carrier device adapted for use with a CD 50 device in accordance with embodiments of the invention. In this example, the CD 50 has a puck-shaped outer housing 51 that is circular in shape that include a circular protruding portion 53 in which the charging coil is at least partly disposed. The carrier 1 is defined by a frame 2 having a circular opening 3 through which the circular portion 53 can be inserted and mounted into the carrier 1. The carrier 1 includes multiple tabs 5, for example three tabs, disposed circumferentially about the frame 2 and extending laterally outward from the opening in which the CD 50 is mounted. Each tab includes an adhesive surface 6 having an adhesive for adhering the carrier to the skin of the patient upon contact. The adhesive is a biocompatible pressure-sensitive adhesive having sufficient adhesive strength to affix the carrier to the patient's skin and support the CD 50 mounted in the carrier 1 for at least a duration of time required to fully charge the device, Durations of charging may be within a range of about 30 minutes to five hours, typically about 2 hours or less.

In another aspect, the carrier 1 includes a mounting interface 4 by which the CD 50 is releasably coupled with the carrier 1. In some embodiments, the mounting interface 4 engages a corresponding mounting feature 54 of the CD 50 so as to securely couple the CD 50 within the carrier 1 while still allowing rotation of the CD 50 relative the charging device. In this example, the mounting interface 4 is a lip or ridge and the corresponding mounting feature 54 is a groove extending about the circular protruding portion 53. The CD 50 is releasably coupled with the carrier 1 in preparation for charging by inserting the circular protruding portion 53 through the mounting hole 3 until the lip 4 is fittingly received within a corresponding groove 54. It is appreciated that since carrier couples with CD along the mounting interface disposed about the circular protruding portion that such a carrier could be used with a CD having an upper housing designed in various other shapes, for example the CD in FIG. 6C or a CD having an upper housing that is non-circular in shape.

FIG. 7B shows an alternative carrier or attachment device comprising a band 9 adapted for use in affixing the CD at a desired position and/or alignment on the patient for charging. Such a band can be configured according to various differing dimensions depending on where the desired affixation location is on the patient's body. For example, for charging of an IPG implanted in a lower back of the patient, the band may be dimensioned as a band having dimensions similar to a belt so as to extend, at least partly, about a patient's waist while supporting the CD at the proper location and/or alignment at the lower back. For other neurostimulation therapies where the IPG is implanted in various other locations, for example an upper arm or chest, the band 9 may be dimensioned as an upper arm band or as a holster to extend across the chest.

FIG. 7C shows yet another alternative carrier comprising an adjustable belt 9' having coupling features 9a and 9b at opposing ends that allow a patient to adjust the belt as desired, typically to fit about their mid-section. Belt 9' can be formed of a breathable and stretchable fabric so as to increase comfort to the patient during charging. Coupling features 9a, 9b can be interfacing features (e.g. snaps, hook and loop, Velcro®), or any suitable coupling means. Belt 9' further includes an circular aperture 3 through which the protruding circular portion 53 of CD 50 can be inserted so that, when the belt is worn, CD 50 can be maintained in a lower back region for charging of an implanted IPG for the duration of charging. This location is particularly applicable to a sacral neuromodulation system as described herein, although it is appreciated that such a belt could be used on a chest or in various other locations as needed for various other types of treatment systems. Belt 9' can include a semi-rigid or rigid frame 2 disposed about circular aperture 3 that includes a mounting interface 4 that releasably couples with a corresponding interface of CD 50 (e.g. snap-fit or tongue-in-groove interface). In this embodiment, mounting interface 4 is axisymmetric about a normal axis through a center of the circular aperture such that CD 50 can be rotated, preferably by 180 degrees or more, to allow rotation of CD 50 while coupled within belt 9'. As in other embodiments described herein, mounting interface can be configured with sufficient resistance to maintain a position of CD held within, once CD is rotated into a desired position.

Figure 8A:
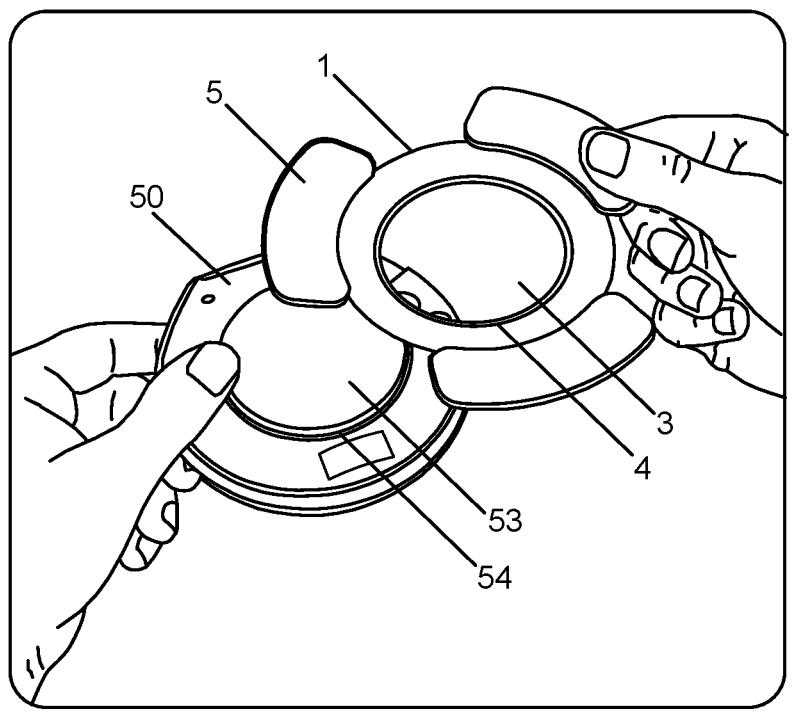
FIGS. 8A-8B show manual coupling of an adhesive carrier device having adhesive tabs to the portable charging device in FIG. 6C, in accordance with aspects of the invention.
Figure 8B:
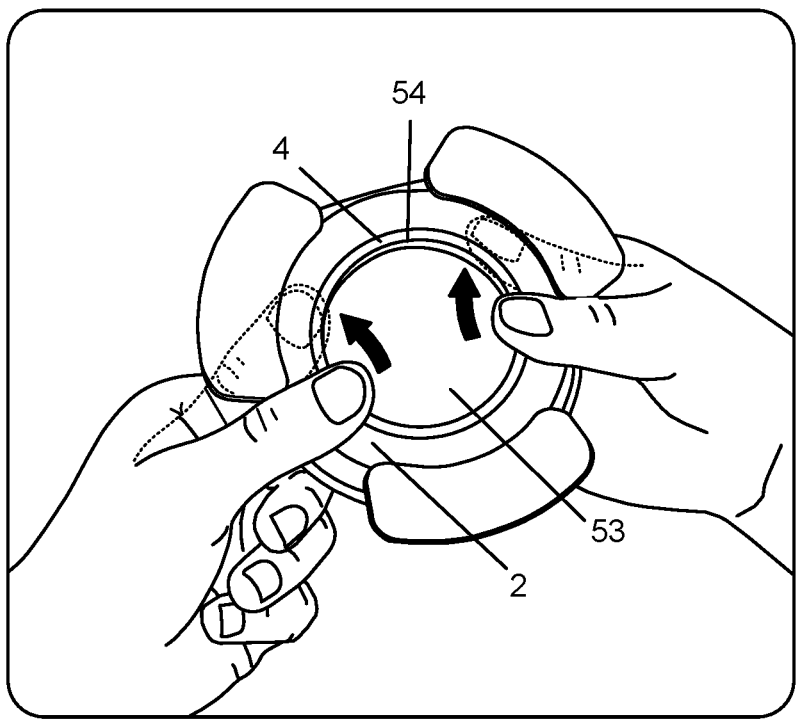

FIGS. 8A-8B shows a patient mounting an example CD 50 within carrier 1, similar to that shown in FIG. 7A. The patient positions carrier 1 with the adhesive surface of the tabs 5 facing away from the CD 50 then inserts the protruding circular bottom portion 53 of CD 50 through the circular aperture 3 of carrier 1. With two hands, the user can then press against both the upper puck-shaped housing of CD 50 and the carrier frame 2 until the mounting interface 4 snaps into the corresponding interface 54 of CD 50. The patient can then press on tabs 50 to move frame 2 into the inverted configuration, if not already within the inverted configuration. A liner disposed over each of the adhesive portions of tabs 5 can then be removed and the planar engaging surface of the circular protruding portion 53 of CD 50 can then be applied to the body and positioned, as described further below.

Figure 8C:
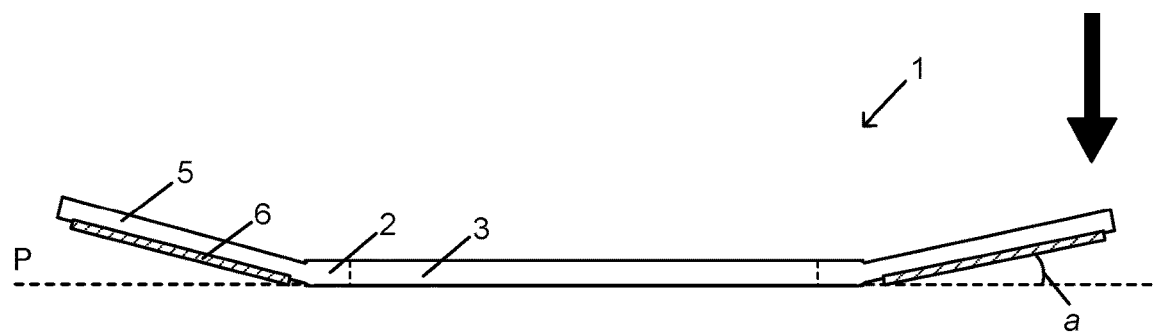
FIGS. 8C-8D show cross-sections of an adhesive carrier device having adhesive tabs in a first position and a second position, in accordance with aspects of the invention.
Figure 8D:
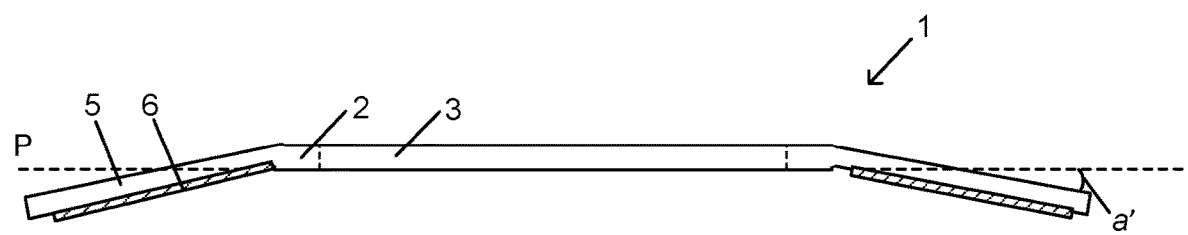

FIGS. 8C-8D shows a cross-section of an adhesive carrier device, similar to that of FIG. 7A, having a frame 2 with a mounting hole 3 extending therethrough and multiple tabs 5 extending laterally outward from the frame 2. The tabs are movable between a first position, shown in FIG. 8C, and a second position, shown in FIG. 8D. As shown in FIG. 8C, the tabs in the first position extend upwards away from the plane P along which the frame 2 of the carrier extends. The tabs in the first position are angled upwards by angle a, which is typically 90 degrees or less, preferably about 45 degrees or less, even more preferably about 30. This upwards angling provides clearance for the CD 50 mounted in the carrier through hole 3 while maintaining the adhesive surface 6 spaced away from the patient's skin when the CD mounted within the carrier 1 is placed on the patient's skin during initial positioning of the CD. FIG. 8D shows the carrier 1 with the tabs 5 in the second position extending towards an opposite direction relative the plane P so as to engage a skin of the patient with the adhesive portions 6. The tabs in the first position are angled downwards by angle a', which is less than 45 degrees, preferably about 30 degrees or less, so as to engage the patient's skin while maintaining the CD mounted therein against the patient's skin.

In one aspect, the carrier includes one or more tabs are formed of a material sufficiently stiff to maintain the first position and the second position when static, yet sufficiently flexible to bend slightly so as to conform to the skin of the patient when in the second position so as to maintain the CD 50 mounted in the carrier 1 against the patient's skin for the duration of charging.

In one aspect, the carrier includes a spring-type mechanism or feature that facilitate ready deployment of the multiple adhesive tabs into engagement with a skin of the patient when the charger device is in a suitable position for charging, as may be indicated by an audible and/or haptic signal from the charging device. Such a configuration is advantageous in a sacral neuromodulation system in which the IPG is implanted in a lower back region and the patient is positioning the charging device in the lower back region with a single hand. In response, to an audible and/or haptic signal output from the charging device that indicates a suitable position for charging, the patient can effect deployment of multiple adhesive tabs by the spring-type mechanism or feature of the charging device carrier. This action can be effected by a pressing against the carrier with a finger of the single hand, for example by depressing a button or lever of the carrier or by pressing against a single tab. In some embodiments, the spring-type feature is provided by the design of the carrier frame itself. The carrier frame can comprise a semi-rigid or rigid material having a standard configuration and an inverted configuration, the frame resiliently springing toward the standard configuration from the inverted configuration.

In one such embodiment, the carrier 1 comprises a frame configured with a standard configuration, in which the tabs 5 are in the second position, and an inverted configuration, in which the tabs 5 are in the first position. Applying a slight force to one or more tabs in the first position in a direction of the arrow shown in FIG. 8C, causes the tabs 5 to rapidly move or spring from the first position to the second position. In some embodiments, the tabs are interconnected through the frame such that application of this force to one tab causes the carrier to move from the inverted configuration to the standard configuration much in the same way that an inverted contact lens springs from an inverted state to its standard shape. In some embodiments, the tab may be continuous about the frame and sufficiently flexible to move between the standard configuration and an inverted configuration. Such a configuration is advantageous as it allows a patient to place the CD 50 mounted in the carrier 1 and position the CD 50 over the implanted device 10 with a single hand and by application of the slight force to the tab with a finger of the same hand, effect rapid movement of the tabs from the first position to the second position, thereby engaging the adhesive surfaces 6 with the patient skin and affixing the carrier and CD at the desired location. The patient can then align the CD 50 with the implanted device 10 by rotating the CD 50 mounted in the carrier 1 affixed to the patient's skin with the same hand.

Figure 9A:
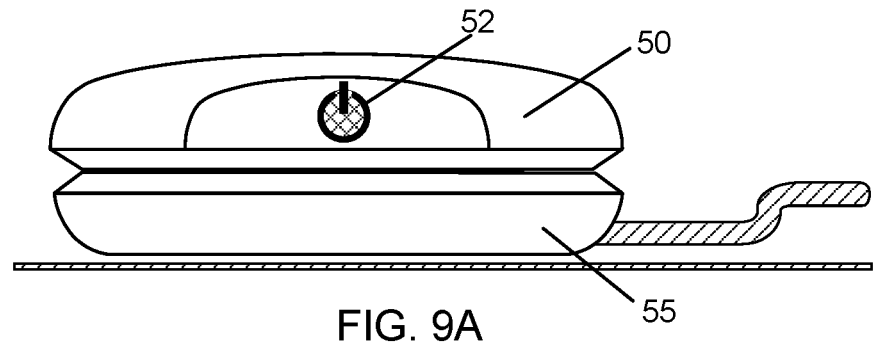
FIGS. 9A-9F illustrate a method of transcutaneously charging an implanted medical device using a carrier device, in accordance with aspects of the invention.
Figure 9B:
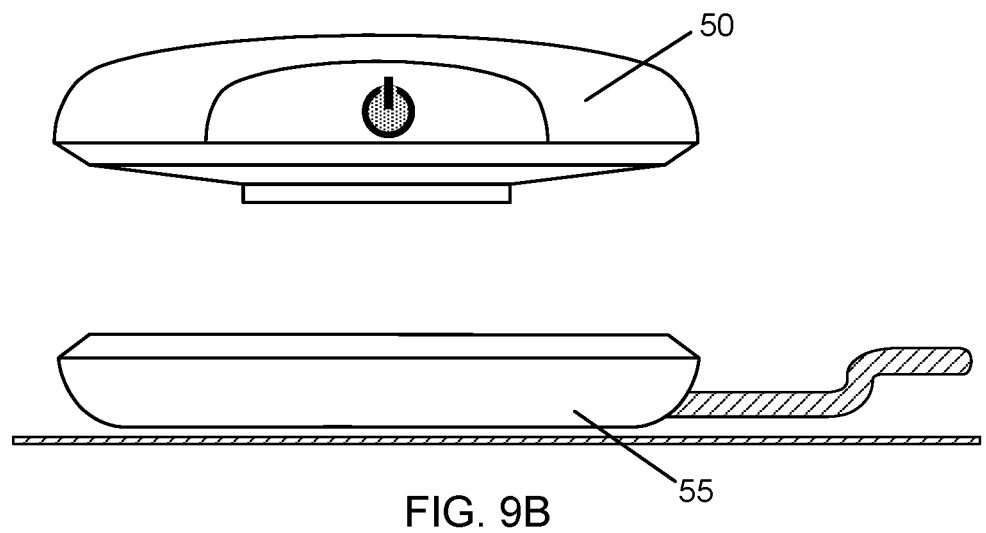
Figure 9C:
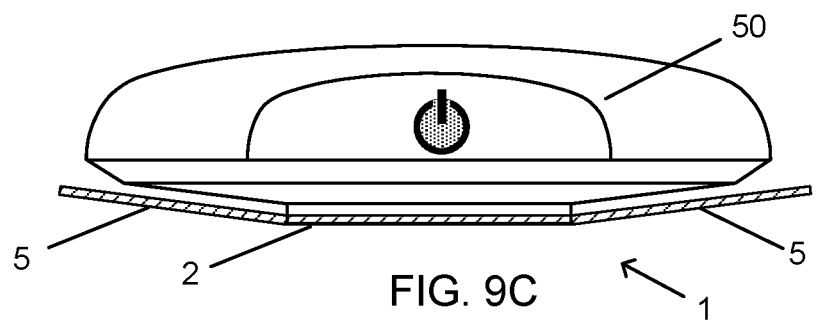
Figure 9D:
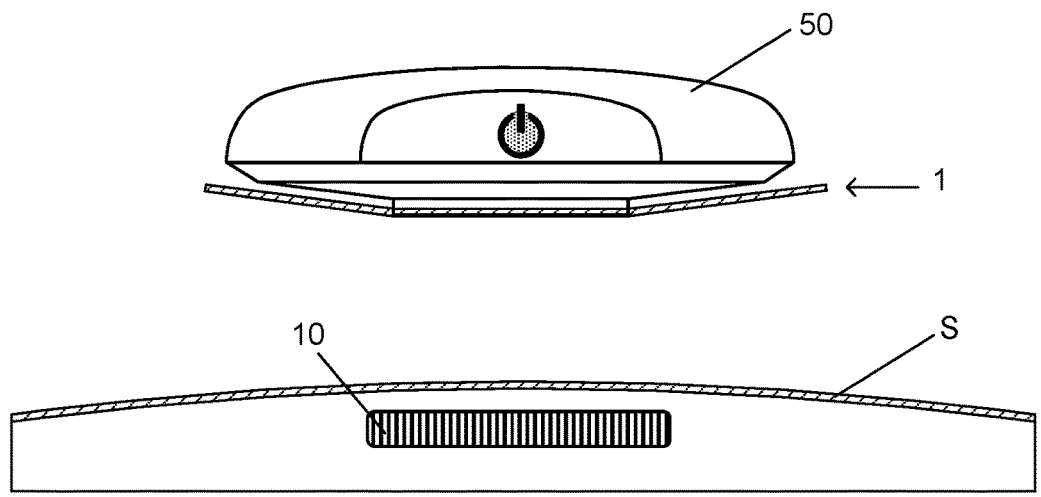
Figure 9E:
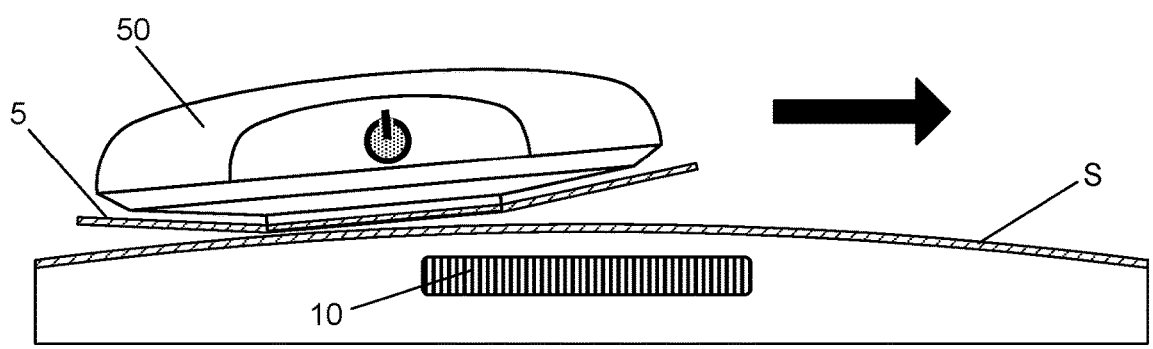

FIGS. 9A-9F illustrate a method of charging using a CD mounted in a carrier 1, in accordance with embodiments of the invention described herein. FIG. 9A depicts the CD 50 resting in its charging station 55 with the visual status indicator 52 showing that the device is charged and ready to charge an implanted device (e.g. green light). Upon removal of the CD 50 from the charging station 55, as shown in FIG. 9B, the CD automatically turns on. The user than releasably couples or mounts the CD 50 within an adhesive carrier device 1 by inserting the CD through a frame 2 of the carrier 1 such that the circular portion of CD extends through the frame 2 while the movable tabs 5 are disposed in the first position, as shown in FIG. 9C. With the CD 50 properly mounted within the carrier 1, the patient removes any film present over the adhesive portions 6 of the tabs and brings the CD 50 towards the implanted device 10, as shown in FIG. 9D. The patient then places the portion of the CD protruding through the carrier 1 in contact with the patient's skin S in the general vicinity of the implanted device 10, as shown in FIG. 9E. In some embodiments, the CD detects the presence of the nearby IPG 10 and may output a user feedback, such as a visual, audio or haptic indicator, that the IPG 10 is in range but off target.

Figure 9F:
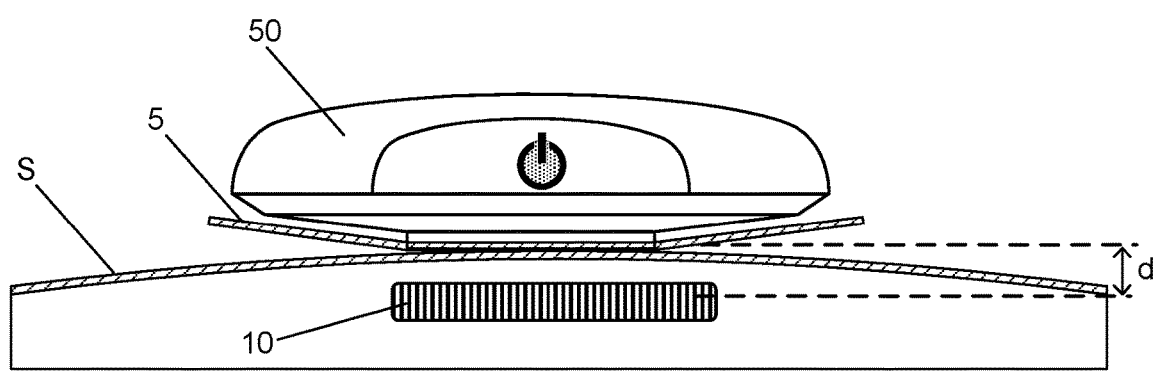

As shown in FIG. 9E, the patient then positions the CD 50 over the IPG 10 by moving the CD along the skin S while the tabs 5 of the carrier are in the first position such that the adhesive portions 6 are spaced away from the patient's skin to avoid affixation to the patient until the CD is properly positioned. Once the CD is properly positioned over the IPG 10, as shown in FIG. 9F, the CD may output user feedback that indicates the CD is at the optimum position for charging. The user feedback will typically be an audio or haptic alert since the patient may not be able to see the visual indicator when the CD is being adhered to a patient's lower back. When properly placed, the distance d between the charging coil in the CD 50 is minimized. In many applications, such as a sacral neuromodulation treatment, the IPG 10 is implanted at a depth of about 3 cm such that the distance d between the charging coil and IPG 10 is about 3 cm when the CD 50 is maintained against the skin with the adhesive carrier.

Figure 10:
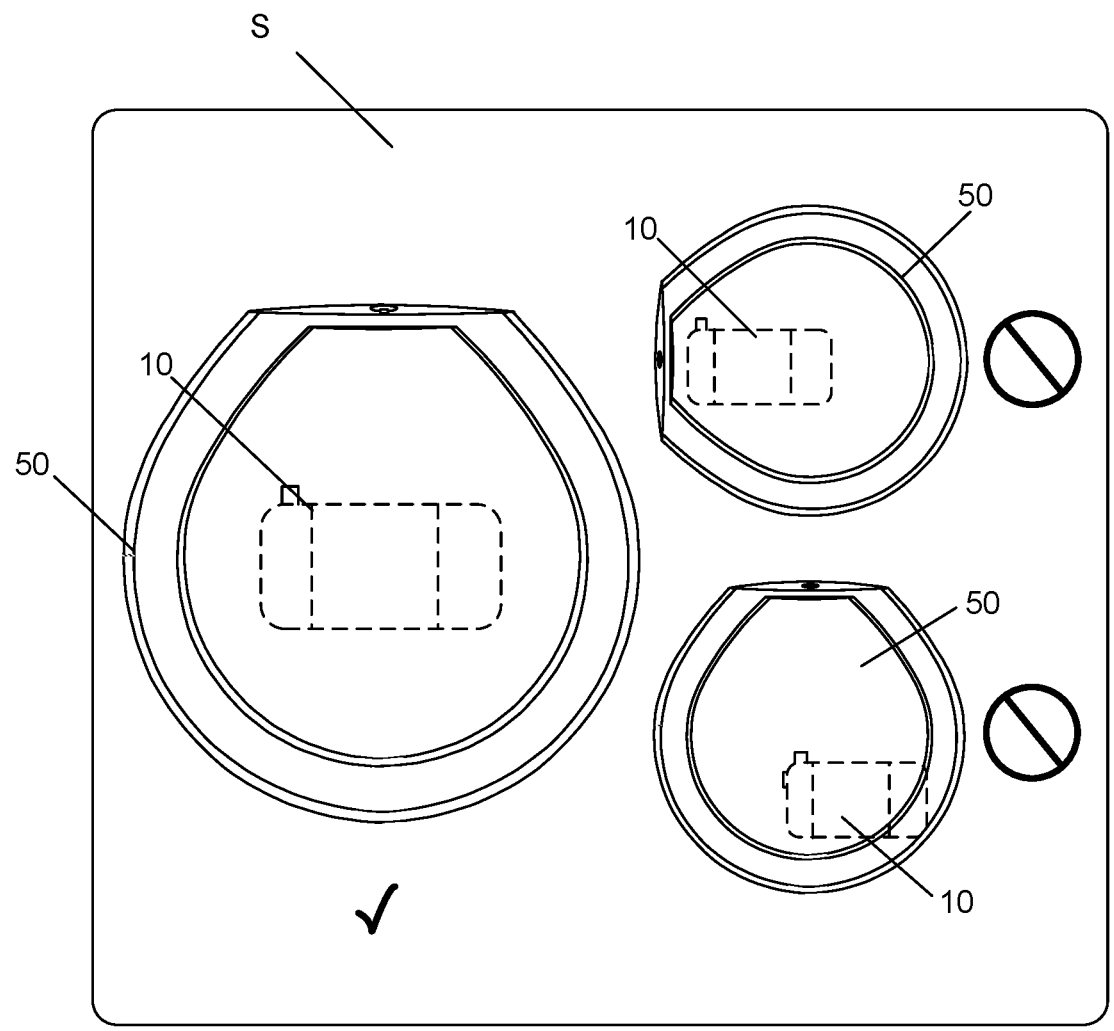
FIG. 10 illustrate examples of charging device placement over an implanted IPG, in accordance with aspects of the invention.

FIG. 10 shows an overhead view of several different alignment of CD 50 over an implanted IPG 10, shown in dashed lines. In this embodiment, the position of optimal charging is the CD 50 directly over the IPG 10 in a particular rotational alignment. Examples of unsuitable positions, which can be indicated by audible/haptic signals or lack of user feedback signals, are shown at right. It is appreciated that, in some embodiments, even if the IPG 10 is not quite in the optimal alignment, CD 50 can still signal that proximity is sufficient for charging, although less than optimal alignments can require longer charging periods.

Figure 11A:
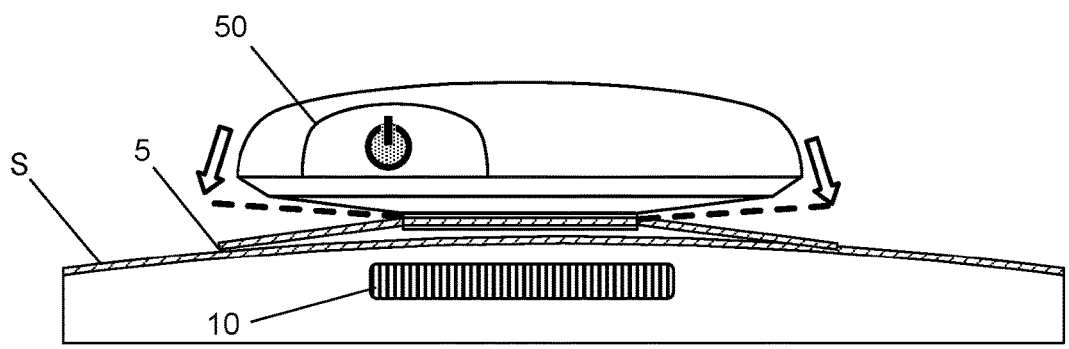
FIGS. 11A-11C illustrate a method of transcutaneously charging an implanted medical device using a carrier device, in accordance with aspects of the invention.
Figure 11B:
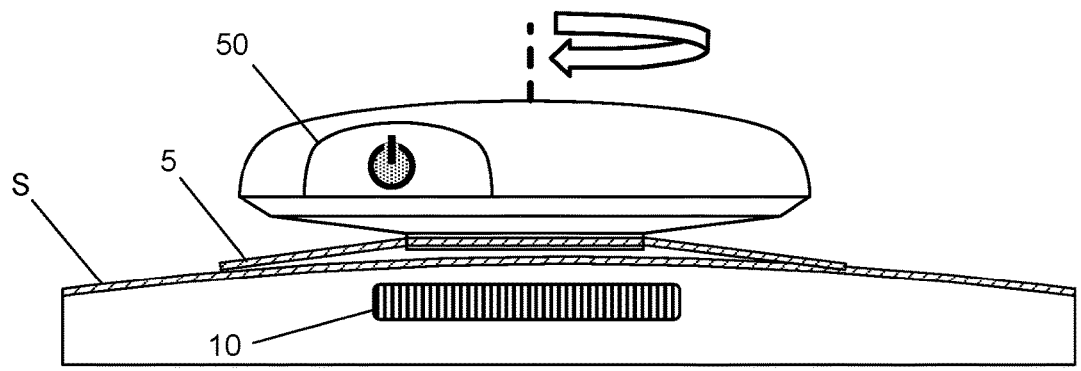
Figure 11C:
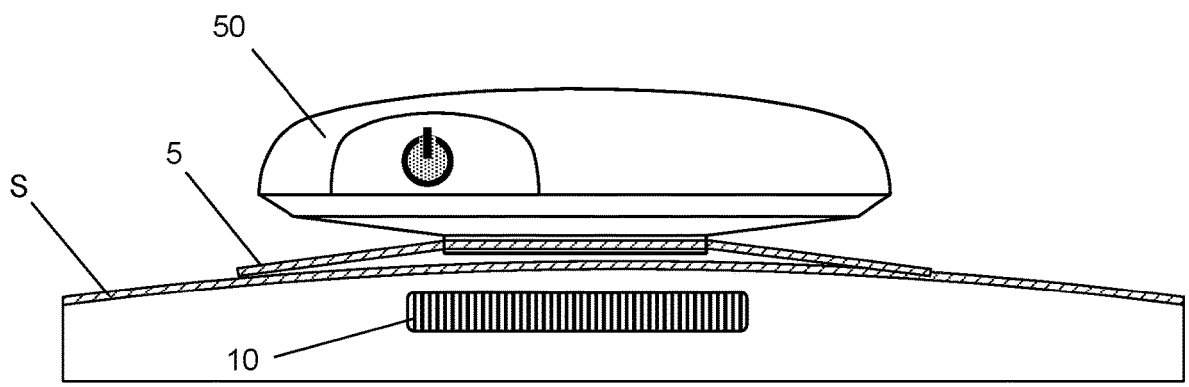

FIGS. 11A-11C illustrate steps taken once the lateral positioning of the CD 50 is performed, as described in FIGS. 9D-9F. Once properly positioned, the patient affixes the CD 50 to their skin by moving the tabs 5 of the carrier 1 from the first position to the second position so that the adhesive surfaces engage the skin of the patient. This is typically done while the patient holds the CD against the skin with the palm of their hand by flipping an upper edge of a tab downwards in the direction of the arrows shown in FIG. 11A, which moves the tabs to a second position that engages the skin of the patient, thereby affixing the CD to the patient's skin S at the proper charging position over the IPG 10, as shown in FIG. 11B. The patient can then remove the support of their hand and the adhesive surfaces hold the CD in place.

Figure 12:
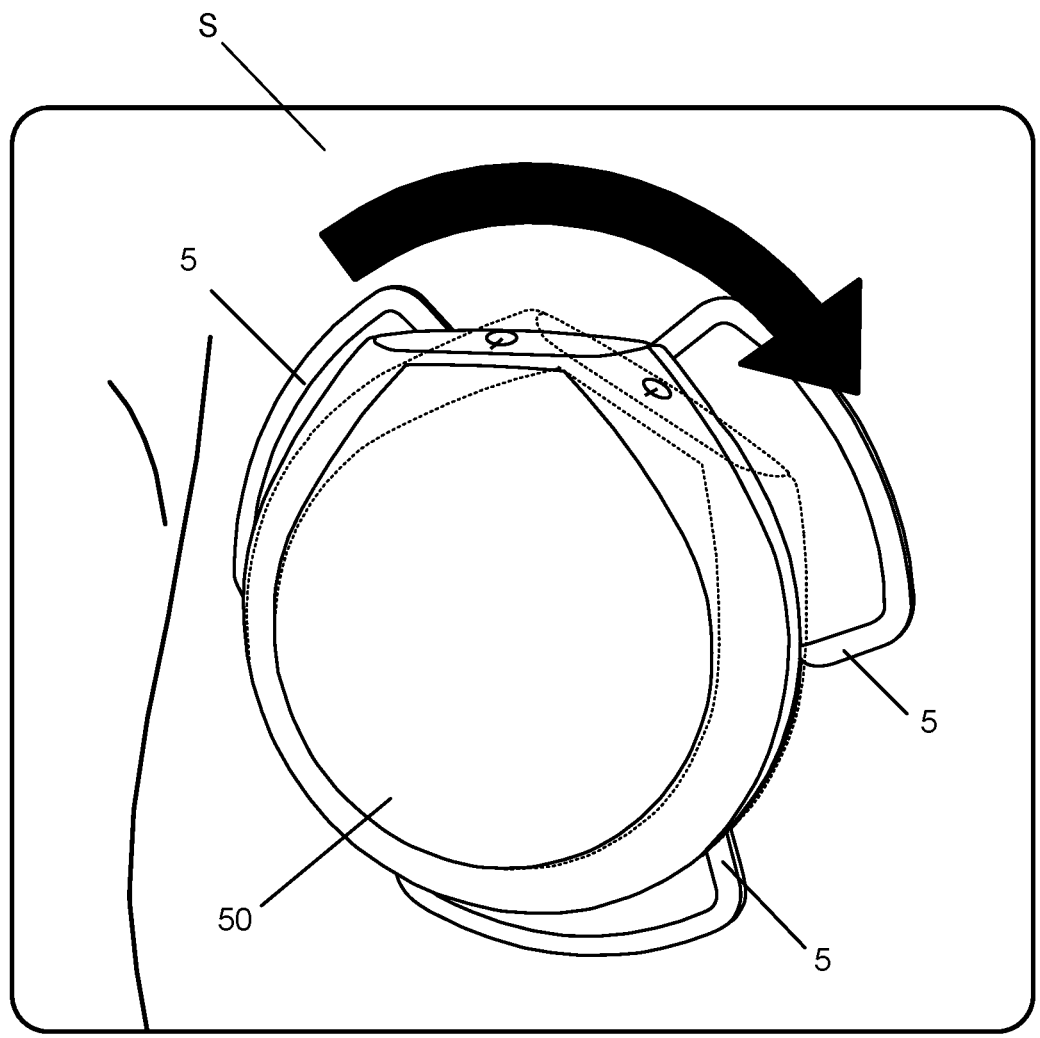
FIG. 12 illustrate a method of transcutaneously charging an implanted medical device by rotating the device to provide optimal alignment, in accordance with aspects of the invention.

Once the CD is properly positioned and affixed to the skin of the patient, the patient can then adjust the rotational alignment of the CD. In one aspect, the carrier is configured such that the CD can be manually rotated while mounted within, yet sufficiently secured such that the CD does not rotate when the CD is static, that is, when no moment forced are applied to the CD. This may be accomplished by providing a mounting interface that allows rotation but provides enough friction to prevent undesired rotation when the device is not being manually rotated by the patient. As shown in FIG. 11B, the patient rotates the CD 50 within the carrier until the CD is properly aligned, as detected by the CD and communicated to the patient through user feedback. Typically, this user feedback is a second haptic and/or audio alert. This alert may be different or the same as the first alert. The patient then allows the CD to remain in place for a duration of time sufficient to allow charging of the device, which is typically at least an hour, such as about two hours. In some embodiments the CD is configured to provide user feedback, such as a third alert, to communicate to the patient that charging is complete and the CD can be removed and the carrier disposed of. FIG. 12 shows an overhead view of rotational adjustment of CD 50 while tabs 5 of carrier remain securely adhered to a patient's skin S.

Figure 13:
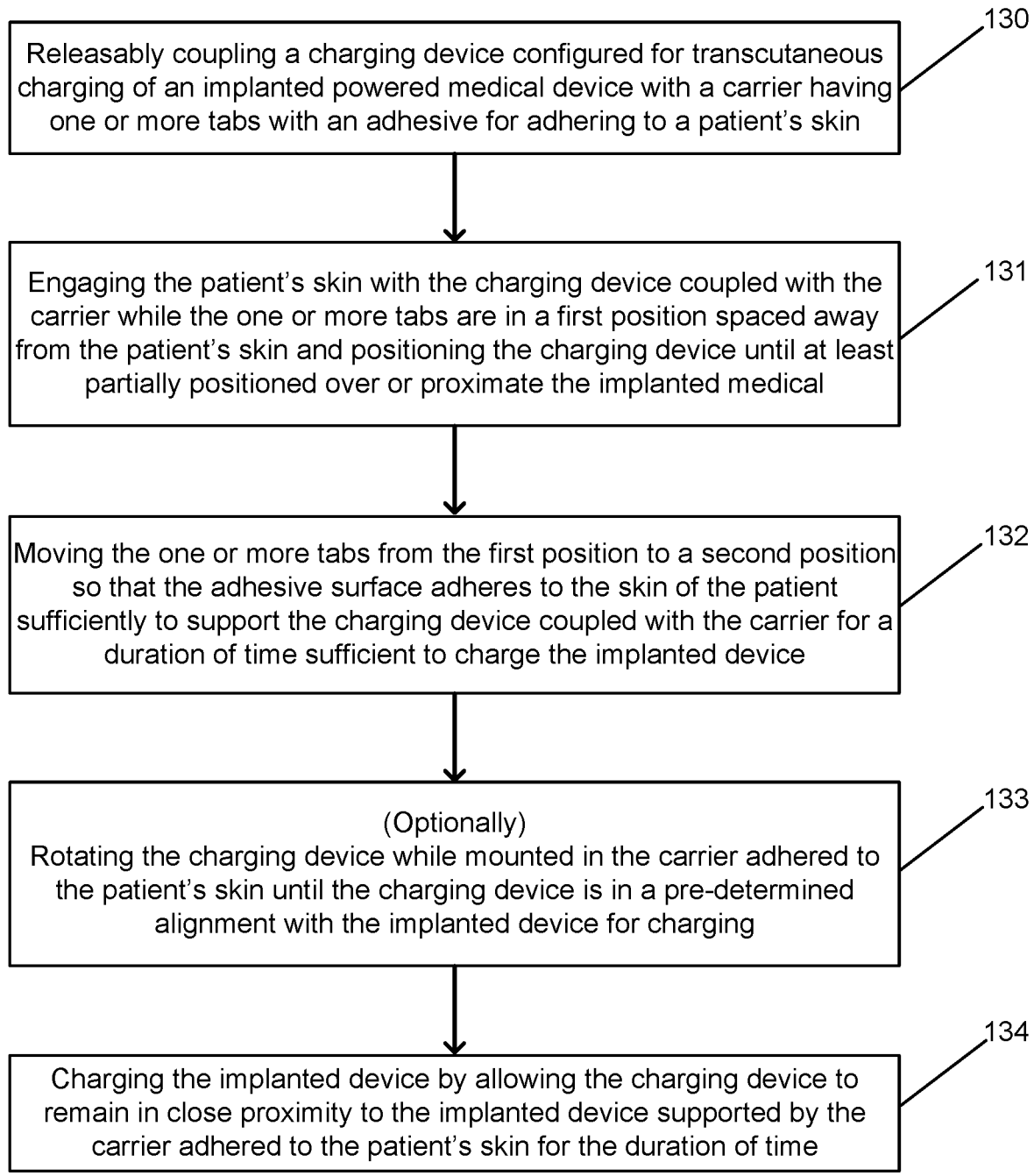
FIG. 13 schematically illustrate a method of transcutaneously charging an implanted medical device using a carrier device, in accordance with aspects of the invention.

FIG. 13 illustrates a method of charging using an adhesive carrier in accordance with embodiments of the invention. The method includes steps of: releasably coupling a CD configured for transcutaneous charging of an implanted powered medical device with a carrier having one or more tabs with an adhesive for adhering to a patient's skin 130; engaging the patient's skin with the charging device coupled with the carrier while the one or more tabs are in a first position spaced away from the patient's skin and positioning the charging device until at least partially positioned over or proximate the implanted medical 131; moving the one or more tabs from the first position to a second position so that the adhesive surface adheres to the skin of the patient sufficiently to support the CD coupled with the carrier for a duration of time sufficient to charge the implanted device 132; optionally, rotating the charging device while mounted in the carrier adhered to the patient's skin until the charging device is in a pre-determined alignment with the implanted device for charging 133; and charging the implanted device by allowing the charging device to remain in close proximity to the implanted device supported by the carrier adhered to the patient's skin for the duration of time 134. In some embodiments, the CD may be configured to provide charging regardless of the rotational alignment or may be configured to adjust the rotational alignment of the charging coil as needed such that manual alignment by the patient may not be required.

Figure 14A:
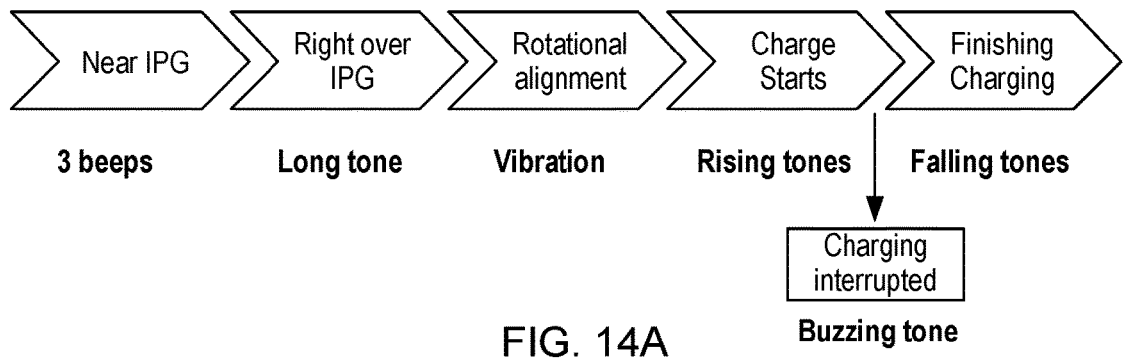
FIGS. 14A-14C schematically illustrate methods of transcutaneously charging an implanted medical device facilitated by use of various indicators or alerts from the charging device, in accordance with aspects of the invention.
Figure 14B:
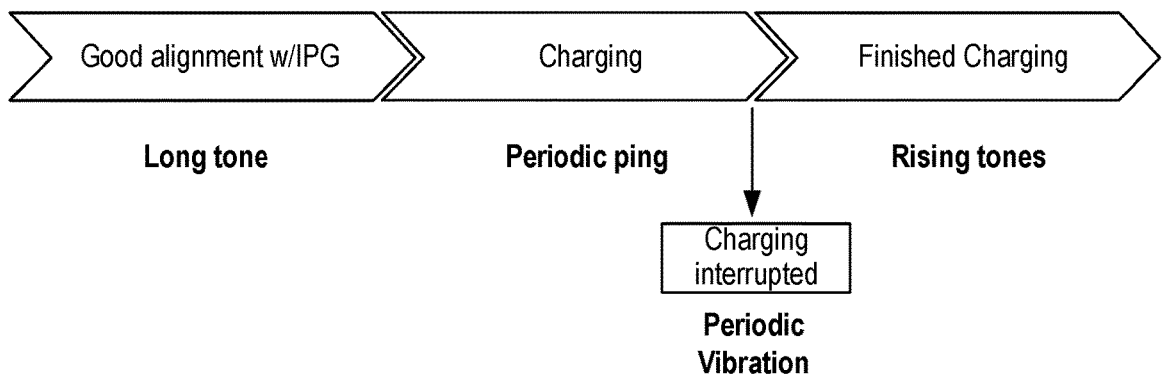
Figure 14C:
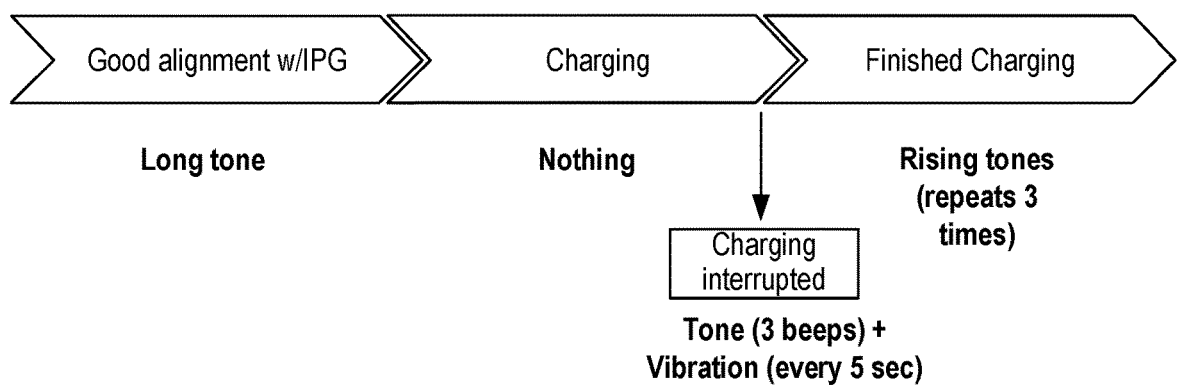

FIGS. 14A-14C illustrate schematics that represent differing charging device configurations that provide indicator or alerts to the patient to facilitate charging of the implanted medical device by the charging device. Each configuration outputs to the patient differing indicators, typically audio and/or haptic alerts) that communicate various aspects of the charging method to the patient. Typically, the configuration includes unique indicators that indicate any or all of: a proximity of the charging device to the implanted device, an alignment of the charging device relative the charging device that is suitable for charging, an interruption in charging, and completion of charging.

FIG. 14A illustrates a configuration that includes a first indicator, such as three audible beeps, to indicate proximity of the charging device relative the IPG; a second indicator, such as a long or sustained tone, to indicated that the charging device is directly over the IPG; a third alert, such as a haptic vibration, to indicate suitable rotational alignment of the charging device relative the IPG; and a fourth alert, such as rising audible tones, to indicate that charging has begun. A fifth alert, such as a buzzing tone, can be used to indicate that charging has been interrupted. In any of the embodiments described, after interruption is indicated, any of the preceding indicators described can be used as needed, for example, if the charging device must be re-positioned or re-aligned to resume charging. A sixth alert, such as falling tones, can be used to indicate that charging is completed. In any of the embodiments described herein, each of the above alerts is provided by the portable charging device based, at least in part, on measurements or determinations by the charging device.

FIGS. 14B-14C illustrate additions configurations having a more streamlined use of indicators than that of the configuration in FIG. 14A. The charger device configuration of FIG. 14B utilizes a first indicator, such as a long tone, to indicate an alignment of the charging device with the IPG that is suitable for charging; a second indicator, such as a periodic ping, to indicate that charging is taking place; a third indicator, such as a periodic vibration, to indicate that charging has been interrupted; and a fourth indicator, such as rising tones, to indicate that charging has been completed. The charger device configuration of FIG. 14C utilizes a first indicator, such as a long tone, to indicate an alignment of the charging device with the IPG that is suitable for charging; a second indicator, such as a combination of periodic vibration and audible tones (e.g. three beeps and vibration repeating every five seconds), to indicate that charging has been interrupted; and a third indicator, such as a series of audible tones (e.g. a repeating series of rising tones), to indicate that charging has been completed. It is appreciated that the above described embodiments are illustrative and that such configurations can utilize various differing types of alerts or combinations thereof in order to communicate an aspect of the charging process or methods to a patient.

Figure 15:
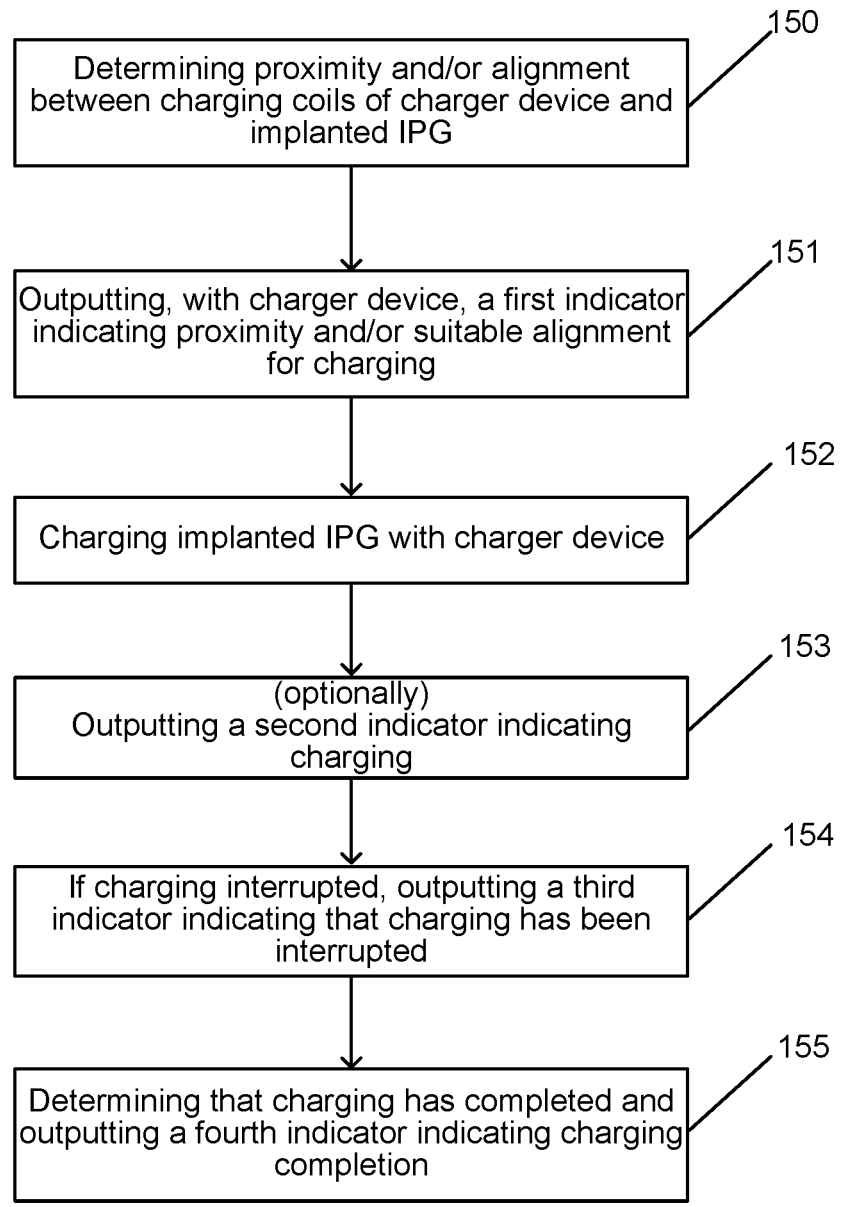
FIG. 15 schematically illustrates a method of transcutaneously charging an implanted medical device using a charging device that outputs differing indicators to the patient, in accordance with aspects of the invention.

FIG. 15 illustrates a method of transcutaneously charging an implanted medical device with a portable charging device facilitated by use of the various indicators, in accordance with various embodiments. In this example, such a method includes: determining proximity and/or alignment between charging coils of charger device and implanted IPG 150; outputting, with charger device, a first indicator indicating proximity and/or suitable alignment for charging 151; charging implanted IPG with charger device 152; optionally, outputting a second indicator indicating charging 153; if charging interrupted, outputting a third indicator indicating that charging has been interrupted; and determining that charging has completed and outputting a fourth indicator indicating charging completion 155.

Figure 16:
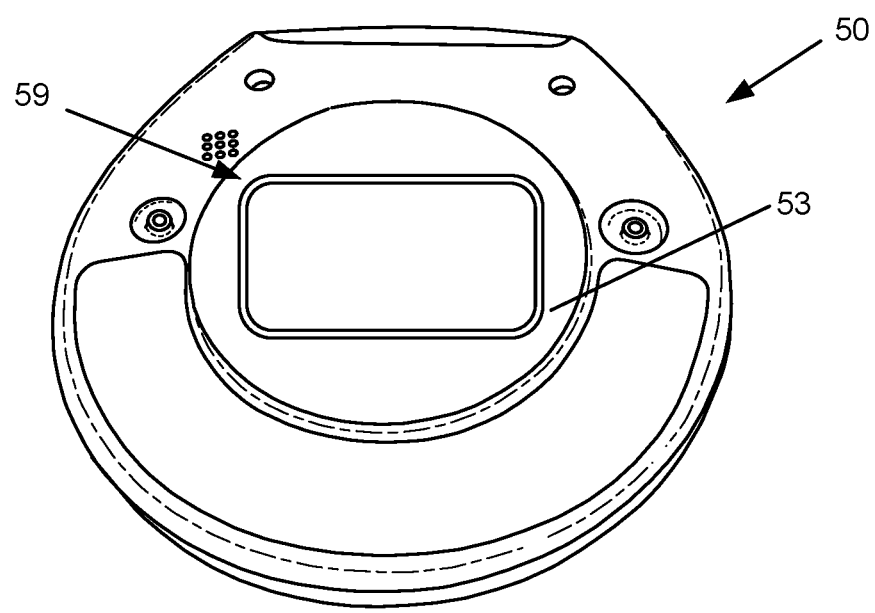
FIG. 16 illustrates a charging device having a graphical indicator that represents a target alignment of the charging device relative the implanted medical device, in accordance with aspects of the invention.

FIG. 16 illustrates a portable charging device 50 having a protruding circular portion 53 on which is disposed an indicator graphic 59 to visually represent a target alignment of charge device 50 relative the IPG. Such an indicator graphic 59 can be used as a training tool and a reminder to the patient to enable consistent, accurate alignment when charging. In this embodiment, indicator graphic 59 graphically represents the size and shape of the IPG in the target orientation by depicting an outline of the IPG. The graphic 59 is provided on a planar surface of protruding circular portion 53 that engages with a skin of the patient. While in this embodiment, graphic 59 is shown as an outline of the IPG on a skin engaging surface of the circular portion 53, it is appreciated that such a graphic indicator could be included on various other surfaces (e.g. top or opposing surface) and can include various other graphics (e.g. arrows, text) to represent a target alignment of the charging device on the patient.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of transcutaneously charging an implanted medical device in a patient, the method comprising:
removably coupling a portable charging device having a housing and a charging coil disposed therein with a carrier having a frame with a plurality of tabs extending therefrom, wherein each of the plurality of tabs includes an adhesive surface, wherein the adhesive surface of each of the plurality of tabs is not in contact with a surface of the charging device, wherein the carrier is resiliently invertible between an inverted configuration and a standard configuration, wherein
in the inverted configuration, the plurality of tabs are in a first position configured to be spaced away from a skin surface of the patient, and
in the standard configuration, the plurality of tabs are in a second position configured to be urged against the skin surface of the patient;
non-invasively engaging a bottom surface of the charging device directly against the skin surface of the patient while mounted within the carrier while the carrier is in the inverted configuration;
positioning the charging device, while the carrier is in the inverted configuration with the plurality of tabs disposed in the first position, until the charging device is at least partially positioned over or proximate the implanted medical device; and
resiliently springing the carrier from the inverted position to the standard configuration, by application of a force to one or more tabs of the plurality, so that the respective adhesive surfaces of all of the plurality of tabs contact and adhere to the skin surface of the patient to support the charging device coupled with the carrier for a duration of time to charge the implanted medical device.

2. The method of claim 1, wherein the carrier is formed of a semi-rigid or rigid material such that the carrier resiliently springs between the inverted configuration in which all of the plurality of tabs are disposed in the first position and the standard configuration in which all of the plurality of tabs are disposed in the second position.

3. The method of claim 2, wherein the one or more tabs comprise a first tab, a second tab, and a third tab, the first tab, the second tab and the third tab being operatively coupled to each other such that the application of force to any of the tabs while the carrier is in the inverted configuration causes the first tab, the second tab, and the third tab to resilient spring from the first position to the second position.

4. The method of claim 2, wherein the plurality of tabs are coupled to a spring mechanism that is configured to facilitate inversion of the plurality of tabs from the first position to the second position.

5. The method of claim 1, further comprising:
moving the plurality of tabs from the second position to the first position;
repositioning the charging device; and
moving the plurality of tabs from the first position to the second position.

6. The method of claim 1, wherein each of engaging the bottom surface of the charging device with the skin surface of the patient, positioning the charging device, and moving the plurality of tabs to the second position is performed with a single hand of the patient.

7. The method of claim 1, wherein the plurality of tabs extend circumferentially, at least partly, about the frame of the carrier, wherein the frame is circular and includes a mounting interface at which the charging device is removably coupled, the charging device being resiliently received within a snap-fit of the mounting interface so that a protruding portion of the charging device directly contacts the skin of the patient when supported within the carrier on the patient.

8. The method of claim 1, wherein removably coupling the charging device with the carrier comprises securing the charging device to a mounting interface of the carrier, wherein the mounting interface is configured to allow manual rotation of the charging device relative to the carrier.

9. The method of claim 8, wherein the mounting interface is configured with a dimensional fit that provides sufficient friction to prevent undesired rotation when the device is not being manually rotated by the patient.

10. The method of claim 1, wherein positioning the charging device until it is at least partially positioned over or proximate the implanted medical device comprises moving the charging device along the skin surface of the patient near the implanted medical device until the charging device outputs a first alert to the patient indicating that the charging device is properly positioned over or proximate the implanted medical device.

11. The method of claim 10, wherein the first alert comprises an audible alert.

12. The method of claim 10, wherein the first alert comprises a haptic feedback.

13. The method of claim 10, further comprising rotating the charging device relative to the carrier while the plurality of tabs secure the carrier to the skin surface of the patient until the charging device is rotationally aligned with a particular orientation of the implanted medical device.

14. The method of claim 13, wherein each of engaging the bottom surface of the charging device with the skin surface of the patient, positioning the charging device, rotating the charging device relative the carrier, and applying the force to any tab of the plurality is performed with a single hand of the patient.

15. The method of claim 13, wherein rotating the charging device comprises rotating the charging device until the charging device outputs a second alert indicating that the charging device is properly aligned with the implanted medical device.

16. The method of claim 15, wherein the second alert is the same as the first alert.

17. The method of claim 15, wherein the second alert is different from the first alert.

18. The method of claim 17, wherein the second alert comprises an audible alert that is different from the first alert.

19. The method of claim 17, wherein the second alert comprises a haptic feedback that is different from the first alert.

20. The method of claim 13, further comprising:
removing the carrier and charging device from the skin surface of the patient after a third alert is output by the charging device, wherein the third alert indicates that charging is complete.

21. The method of claim 1, wherein the carrier is integrally formed of a polymeric material that is semi-rigid or rigid.

22. The method of claim 1, wherein the implanted medical device is configured for sacral neuromodulation and is implanted within the lower back or upper buttock region of the patient and where the charging device is configured to be positioned and secured with the carrier by a single hand of the user.

* * * * *